(12) United States Patent
Craig

(10) Patent No.: US 6,440,988 B1
(45) Date of Patent: Aug. 27, 2002

(54) USE OF AGONISTS OR ANTAGONISTS OF THE 5-HT$_7$ RECEPTOR TO TREAT DISORDERS OF THE BLADDER

(75) Inventor: Douglas A. Craig, Emerson, NJ (US)

(73) Assignee: Synaptic Pharmaceutical Corporation, Paramus, NJ (US)

(*) Notice: Subject to any disclaimer, the term of this patent is extended or adjusted under 35 U.S.C. 154(b) by 0 days.

(21) Appl. No.: 09/657,665

(22) Filed: Sep. 8, 2000

Related U.S. Application Data (63) Continuation-in-part of application No. PCT/US00/13644, filed on May 17, 2000, which is a continuation-in-part of application No. 09/313,585, filed on May 18, 1999, now abandoned.

(51) Int. Cl.$^7$ .............................................. A61K 31/44
(52) U.S. Cl. ...................................... 514/285; 514/292
(58) Field of Search .................................. 514/285, 292

(56) References Cited

U.S. PATENT DOCUMENTS

| | | | |
|---|---|---|---|
| 5,629,317 A | 5/1997 | Audia et al. | 514/278 |
| 5,643,916 A | 7/1997 | Audia et al. | 514/285 |
| 5,688,807 A | 11/1997 | Audia et al. | 514/285 |
| 5,985,585 A | 11/1999 | Bard et al. | 435/7.21 |
| 6,083,749 A | 7/2000 | Bard et al. | 435/356 |
| 6,300,087 B1 | 10/2001 | Bard et al. | 435/7.21 |

FOREIGN PATENT DOCUMENTS

| | | |
|---|---|---|
| WO | 9524200 | 9/1995 |
| WO | 9729097 | 8/1997 |
| WO | 9735578 | 10/1997 |
| WO | 9749695 | 12/1997 |
| WO | 9500400 | 1/1998 |
| WO | 9924022 | 5/1999 |
| WO | 9959499 | 11/1999 |

OTHER PUBLICATIONS

Kikuchi, C., et al., "Tetrahydrobenzindoles: Selective Antagonists of The 5–HT$_7$ Receptor," *J. Medicinal Chemistry* (1999) 42 (4): 533–525;.

Forbes, I. T., et al., "(R)–3, N–Dimethyl–N–[1–methyl–3–(4–methyl–piperidin–1–yl)propyl ]benzenesulfonamide: The First Selective 5–HT$_7$ Receptor Antagonist," *J. Medicinal Chemistry* (1998) 41 (5):655–657;.

Baxter, G. S., "Novel Discriminatory Ligands For 5–HT$_{2B}$ Receptors," *Behavioral Brain Research* (1996) 73 (1–2): 149–152;.

Baxter, G. S., et al., "SB 204741: A Potent and Selective Antagonist At 5–HT$_{2B}$ Receptors," *Br. J. Pharmacol.* (1995) 114:157P;.

Forbes, I. T., et al., "N–(1–methyl–5–indolyl) N'–(3–methyl–5–isothiazolyl)urea: A Novel , High–Affinity 5–HT$_{2B}$ Receptor Antagonist," *J. Med. Chem.* (1995) 38 (6): 855–857;.

Bonhaus, D. W., et al., "RS–127445: A Selective, High Affinity, Orally Bioavailable 5–HT$_{2B}$ Receptor Antagonist," *Br. J. Pharmacol.* (1999) 127(5): 1075–1082;.

Cushing, D.J., et al., "LY215840, A High–Affinity 5–HT7 Receptor Ligand, Blocks Serotonin–Induced Relaxation In Canine Cornary Artery," *J. Pharmacol. Exp. Ther.* (1996) 277:1560–1566.

*Primary Examiner*—Kevin E. Weddington
(74) *Attorney, Agent, or Firm*—John P. White; Cooper & Dunham LLP (57) ABSTRACT

The present invention provides a method of treating urinary incontinence in a subject which comprises administering to the subject a therapeutically effective amount of a 5-HT$_7$ receptor antagonist or an antagonist that binds to both 5-HT$_7$ and 5-HT$_{2B}$ receptors. The invention also provides a method of treating urinary retention in a subject which comprises administering to the subject a therapeutically effective amount of a 5-HT$_7$ receptor agonist or an agonist that activates both 5-HT$_7$ and 5-HT$_{2B}$ receptors.

18 Claims, 3 Drawing Sheets

FIGURE 1

Figure 2. Correlation of antagonist affinities at stimulated rat bladder ($pK_B$) vs cloned $5\text{-}HT_{2B}$ receptor ($pK_i$)

Figure 3. Correlation of antagonist affinities at stimulated rat bladder (pK$_B$) vs cloned 5-HT$_7$ receptor (pK$_i$)

USE OF AGONISTS OR ANTAGONISTS OF THE 5-HT₇ RECEPTOR TO TREAT DISORDERS OF THE BLADDER This application is a continuation-in-part of PCT International Application No. PCT/US00/13644, filed May 17, 2000, which is a continuation-in-part of U.S. Ser. No. 09/313,585, filed May 18, 1999 now abandoned, the contents of both of which are hereby incorporated by reference into the subject application.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to describe more fully the art to which this invention pertains.

Normal bladder function requires coordinated bladder contraction and urethral sphincter relaxation during the emptying phase and the opposite, bladder relaxation and urethral sphincter contraction, during the filling/storage phase. The occurrence of irregularities in these processes increases with age in males and females and can lead to a variety of disorders of lower urinary tract function, including incontinence and urinary retention.

Incontinence and Urinary Retention

Incontinence is characterized by the involuntary loss of urine. It can be divided generally into two types, stress and urge incontinence. Stress incontinence is characterized by an inability to generate or maintain normal closing pressure at the bladder outlet and urethra. Involuntary urine loss can be provoked whenever the physical stress of everyday activities causes abdominal pressure to rise above the level of the bladder closing pressure; hence the name. The underlying pathology may involve (1) damage to the nerves which send contractile signals to these structures (such as may occur during childbirth), or (2) loss of mass of the urothelium after menopause, or (3) other processes which result in primary muscle weakness or loss of tone to these structures (Wein, 1987; Andersson, 1988).

Urge incontinence, in contrast, involves primarily changes in the function of the main body (detrusor) of the bladder. These changes disrupt the normal manner in which bladder volume/distention is sensed and translated into, first, the desire to void and, ultimately, the neuronal impulses signaling detrusor contraction. Rather than a graded response to bladder distention, patients with urge incontinence experience involuntary leakage preceded by a sensation of urgency and impending urinary loss. A large portion of patients with urge incontinence are shown by urodynamic evaluation to have detrusor instability, characterized by spontaneous, involuntary contractions (Swami and Abrams, 1996). The underlying pathology may involve either the sensory or motor nervous systems innervating the detrusor, or may be associated with inflammation and irritative processes in the bladder muscle, or may be idiopathic (Andersson, 1988).

As the name implies, urinary retention describes a condition in which there is difficulty in voiding. In some instances this may occur as a result of bladder outlet obstruction, as is seen in patients with benign prostatic hyperplasia (BPH). Indeed, chronic bladder outlet obstruction may lead to secondary bladder hyper-reflexia which may persist after correction of the obstruction and may involve remodeling of the neuronal circuitry of the bladder (Swami and Abrams, 1996). Urinary retention in the absence of bladder outlet obstruction may arise from deficits in the same systems as urge incontinence: the neurons or smooth muscle of the detrusor.

Neural Control of the Urinary Bladder

The contractile activity of the lower urinary tract structures is controlled primarily by two neurotransmitter systems (Wein, 1987). Neurons of the sympathetic nervous system innervate the urethra and bladder base, and to a lesser extent the detrusor, releasing the neurotransmitter norepinephrine (NE). The smooth muscle of the urethra and bladder base are endowed with alpha-adrenergic receptors where NE acts to cause contractions. In contrast, adrenergic receptors of the detrusor are of the beta-adrenergic subtype, the activation of which causes relaxation. Thus, activation of the sympathetic nervous system in the bladder promotes urine storage. Parasympathetic neurons innervate the detrusor, but not the bladder base or urethra. Parasympathetic neurons release the neurotransmitters acetylcholine (ACh) and adenosine-5'-triphosphate (ATP) which act, respectively, at $M_3$-muscarinic and $P_{2X}$-purinergic receptors to elicit contractions. Activation of the parasympathetic nervous system, therefore, promotes bladder emptying.

Although these neuronal systems play a key role in the motor activity of the lower urinary tract, other neurotransmitters are involved to varying degrees in different species, and possibly to varying degrees during different pathological states within a given species (e.g. humans). Indeed, Ferguson and Christopher (1996) state that "up to 50% of contractile activity in patients with bladder instability is sensitive to tetrodotoxin (i.e., is of neuronal origin) but resistant to atropine, suggesting that purinergic (i.e., involving the neurotransmitter ATP) or other NANC (non-adrenergic, non-cholinergic) neurotransmission plays a greater role in pathological conditions."

In addition to transmitters stored in and released from terminals of efferent nerves, transmitters of afferent nerves and their receptors are also involved in the control of lower urinary tract function. Tachykinins, such as substance P, neurokinins A and B, and other neuropeptides have been demonstrated in nerves of the lower urinary tract and shown to be able to influence bladder function (Andersson, 1996). Among the 'non-classical' transmitters which have been studied is nitric oxide, which plays a role in the relaxation of the bladder base and urethra during micturition (Werkstrom et al., 1997). One of the more extensively studied classical neurotransmitters in the bladder is 5-hydroxytryptamine (5-HT). In the human detrusor 5-HT has been shown to have multiple effects on bladder contractility. One of the ways in which 5-HT has been shown to affect contractions is by modifying the neuronal release of the primary parasympathetic neurotransmitters, ACh and ATP (see below).

Current Treatments for Micturition Disorders

A variety of pharmaceutical agents have been employed to treat micturition disorders. Drugs used to reduce bladder contractility associated with urge incontinence include muscarinic receptor antagonists, calcium channel blockers, direct smooth muscle relaxants, and beta-adrenergic receptor agonists (Andersson, 1988). In addition, prostaglandin synthesis inhibitors and tricylic antidepressants have been investigated for this purpose (Andersson, 1988). More recently, there has been an interest in developing potassium channel openers, aimed at reducing contractility by hyperpolarizing detrusor smooth muscle cells (Ohnmacht et al., 1996). The most commonly employed therapeutic agents for increasing bladder outlet resistance are the alpha-adrenergic receptor agonists and estrogen (Wein, 1987). The only agents which are effective at increasing detrusor contractions and improving bladder emptying are the muscarinic receptor agonists (Andersson, 1988). Each of these therapies is associated with limited efficacy and unwanted side effects (Andersson, 1988; Wein, 1987).

5-HT in Bladder Function

The physiological role of 5-hydroxytryptamine (5-HT) in bladder detrusor varies widely among different species, with respect to both the nature of response and the receptor subtype involved. For example, 5-HT produces marked contractions mediated by postjunctional $5-HT_2$ receptors in isolated detrusor from cat (Saxena et al., 1985) and dog (Cohen, 1990). Potent direct 5-HT-evoked contractions have also been described for human detrusor strips (Klarskov and Hørby-Petersen, 1986). Although the responses were found to be relatively insensitive to 0.1 μM ketanserin, and therefore not associated with $5-HT_{2A}$ receptor activation, the identity of the subtype involved remains to be determined. In contrast, direct contractile effects of 5-HT are absent in the bladder body of rat and guinea pig (Cohen and Drey, 1989) and monkey (Waikar et al., 1994). Unlike other species, the monkey bladder expresses postjunctional $5-HT_4$ receptors, activation of which produces relaxation (Waikar et al., 1994).

In addition to these direct effects, 5-HT receptors play a role in modulating the contractile effects of neuronally released ACh and ATP. Thus, it has been reported that 5-HT in the mouse urinary bladder enhances electrically evoked, neuronally mediated contractions via activation of $5-HT_{1B}$ (Holt et al., 1985, 1986; Cleal et al., 1989) and ketanserin-sensitive $5-HT_2$ (Cleal et al., 1989) receptors located prejunctionally. In guinea pig detrusor, activation of prejunctional $5-HT_4$ and $5-HT_{2A}$ receptors leads primarily to an increase in purinergic activity (Messori et al., 1995), while 5-HT-evoked increases in cholinergic activity in guinea pig (Messori et al., 1995), rabbit (Chen, 1990), and cat (Saxena et al., 1985) are mediated by $5-HT_3$ receptors. In addition to $5-HT_3$ receptors, $5-HT_4$ subtypes have been shown to mediate the potentiation of cholinergic, neuronally induced contractions of isolated human detrusor (Corsi et al., 1991; Tonini et al., 1994). Furthermore, Corsi et al. (1991) also described the opposite effect, i.e. inhibition of cholinergic responses induced by micromolar concentrations of 5-HT, and ascribed these to activation of $5-HT_{1-like}$ receptors.

Discovery of $5-HT_7$ and $5-HT_{2B}$ Receptor Function in the Urinary Bladder

The investigations leading to the present invention were inspired by our finding that messenger RNA for the $5-HT_7$ receptor is present in tissue specimens from human (Bard et al., DNA Encoding a Human Serotonin Receptor ($5-HT_{4B}$) And Uses Thereof, U.S. patent application Ser. No. 08/281, 526, now U.S. Pat. No. 6,083,749, issued Jul. 4, 2000) and rat urinary bladders (see below), as well as the localization of the $5-HT_{2B}$ receptor in the rat bladder (see below; PCT International Application Nos. WO 95/24200, WO 97/35578). The "$5-HT_7$ receptor" had previously been known as the "$5-HT_{4B}$ receptor" until it was renamed by the Serotonin Receptor Nomenclature Committee of the IUPHAR (Hoyer et al., 1994). Prior to our investigation, the role of 5-HT in contractile activity of the rat bladder, as opposed to other species (see above) was considered to be insignificant (Cohen and Drey, 1989). In order to ascertain the physiological role of the rat bladder $5-HT_7$ and $5-HT_{2B}$ receptors, we explored the possibility that these receptors may modulate the activity of the parasympathetic nervous system in the bladder. To simulate this condition, we employed an electrical stimulus of sufficient intensity to activate only the intrinsic detrusor neurons. Prior to this study, the effects of 5-HT in electrically stimulated preparations of rat bladder have not been described.

This invention relates to the discovery that activation of $5-HT_7$ receptors in the bladder leads to an increase in the magnitude of contractions mediated by neurotransmitters of the parasympathetic nervous system. In the course of our investigations, we discovered unexpectedly that the $5-HT_{2B}$ receptor subserves the same role in the bladder: i.e., activation of the $5-HT_{2B}$ receptor also leads to an increase in the magnitude of contractions mediated by parasympathetic neurotransmitters. Thus, this document is the first describing the presence and functional role of the $5-HT_7$ receptor in the bladder, the first to describe a role of the $5-HT_7$ receptor in which activation of the receptor causes augmentation of neuronal activity in any physiological system in any species, and the first to describe the functional role of the $5-HT_{2B}$ receptor in the bladder. Hence, the possibility that agents acting at either (a) the $5-HT_7$ receptor alone, or (b) the $5-HT_7$ and $5-HT_{2B}$ receptors in combination may be of value in the treatment of micturition disorders was heretofore unrecognized by those skilled in the art. Because of the key role of parasympathetic neurotransmitters in the control of bladder function, it is proposed that compounds which activate $5-HT_7$ receptors, or both $5-HT_7$ and $5-HT_{2B}$ receptors, will be useful in treating urinary retention, by virtue of their ability to facilitate muscular contractions, thereby promoting more efficient elimination of urine. Conversely, compounds which act to antagonize the actions of 5-HT at $5-HT_7$ receptors or both $5-HT_7$ and $5-HT_{2B}$ receptors, will be useful in treating urinary urge incontinence, by acting to diminish the neurogenic impulses which initiate detrusor contraction.

SUMMARY OF THE INVENTION

The present invention provides a method of treating urinary incontinence in a subject which comprises administering to the subject a therapeutically effective amount of either a $5-HT_7$ receptor antagonist or an antagonist that acts at both $5-HT_7$ and $5-HT_{2B}$ receptors to reduce abnormal neurogenically mediated contraction of the urinary bladder. The invention also provides a method of treating urinary retention in a subject which comprises administering to the subject a therapeutically effective amount of either a $5-HT_7$ receptor agonist or an agonist that acts at both $5-HT_7$ and $5-HT_{2B}$ receptors to increase contraction of the urinary bladder.

The invention provides a method of treating urinary incontinence in a subject which comprises administering to the subject a therapeutically effective amount of a $5-HT_7$ antagonist which binds to the human $5-HT_7$ receptor with an affinity at least ten-fold higher than the affinity with which it binds to each of the human $5-HT_{1A}$, $5-HT_{2A}$, $5-HT_{2C}$, $5-HT_3$, $5-HT_4$, and $5-HT_6$ receptors.

Preferably, the aforementioned $5-HT_7$ antagonist additionally binds to the human $5-HT_7$ receptor with an affinity at least ten-fold higher than the affinity with which it binds to each of the human $5-HT_{1B}$, $5-HT_{1D}$, $5-HT_{1E}$, $5-HT_{1F}$, $5-HT_{5A}$, and $5-HT_{5B}$ receptors.

In an additional embodiment of the invention, the $5-HT_7$ antagonist is also a $5-HT_{2B}$ antagonist which binds to the human $5-HT_{2B}$ receptor with an affinity at least 10-fold higher than the affinity with which it binds to each of the human $5-HT_{1A}$, $5-HT_{2A}$, $5-HT_{2C}$, $5-HT_3$, $5-HT_4$, and $5-HT_6$ receptors.

Preferably, the 5-HT$_7$ antagonist additionally binds to the human 5-HT$_{2B}$ receptor with an affinity at least ten-fold higher than the affinity with which it binds to each of the human 5-HT$_{1B}$, 5-HT$_{1D}$, 5-HT$_{1E}$, 5-HT$_{1F}$, 5-HT$_{5A}$, and 5-HT$_{5B}$ receptors.

The invention also provides a method of treating urinary retention in a subject which comprises administering to the subject a therapeutically effective amount of a 5-HT$_7$ agonist which activates the human 5-HT$_7$ receptor at least ten-fold more than it activates each of the human 5-HT$_{1A}$, 5-HT$_{2A}$, 5-HT$_{2C}$, 5-HT$_3$, 5-HT$_4$, and 5-HT$_6$ receptors.

Preferably, the aforementioned 5-HT$_7$ agonist additionally activates the human 5-HT$_7$ receptor at least ten-fold more than it activates each of the human 5-HT$_{1B}$, 5-HT$_{1D}$, 5-HT$_{1E}$, 5-HT$_{1F}$, 5-HT$_{5A}$, and 5-HT$_{5B}$ receptors.

In an additional embodiment of the invention, the 5-HT$_7$ agonist is also a 5-HT$_{2B}$ agonist which activates the human 5-HT$_{2B}$ receptor at least ten-fold more than it activates each of the human 5-HT$_{1A}$, 5-HT$_{2A}$, 5-HT$_{2C}$, 5-HT$_3$, 5-HT$_4$, and 5-HT$_6$ receptors.

Preferably, the 5-HT$_7$ agonist additionally activates the human 5-HT$_{2B}$ receptor at least ten-fold more than it activates each of the human 5-HT$_{1B}$, 5-HT$_{1D}$, 5-HT$_{1E}$, 5-HT$_{1F}$, 5-HT$_{5A}$, and 5-HT$_{5B}$ receptors.

The invention further provides a method of treating urinary incontinence in a subject which comprises administering to the subject a therapeutically effective amount of an admixture of a 5-HT$_7$ antagonist and a 5-HT$_{2B}$ antagonist, wherein both the affinity with which the 5-HT$_7$ antagonist binds to the human 5-HT$_7$ receptor and the affinity with which the 5-HT$_{2B}$ antagonist binds to the human 5-HT$_{2B}$ receptor are at least ten-fold higher than the affinity with which each antagonist binds to each of the human 5-HT$_{1A}$, 5-HT$_{2A}$, 5-HT$_{2C}$, 5-HT$_3$, 5-HT$_4$, and 5-HT$_6$ receptors.

Preferably, the 5-HT$_7$ antagonist additionally binds to the human 5-HT$_7$ receptor and the 5-HT$_{2B}$ antagonist additionally binds to the human 5-HT$_{2B}$ receptor with an affinity at least ten-fold higher than the affinity with which each antagonist binds to each of the human 5-HT$_{1B}$, 5-HT$_{1D}$, 5-HT$_{1E}$, 5-HT$_{1F}$, 5-HT$_{3A}$, and 5-HT$_{5B}$ receptors.

The invention also provides a method of treating urinary retention in a subject which comprises administering to the subject a therapeutically effective amount of an admixture of a 5-HT$_7$ agonist and a 5-HT$_{2B}$ agonist, wherein both the 5-HT$_7$ agonist activates the human 5-HT$_7$ receptor and the 5-HT$_{2B}$ agonist activates the human 5-HT$_{2B}$ receptor at least ten-fold more than the extent to which each agonist activates each of the human 5-HT$_{1A}$, 5-HT$_{2A}$, 5-HT$_{2C}$, 5-HT$_3$, 5-HT$_4$, and 5-HT$_6$ receptors.

Preferably, the 5-HT$_7$ agonist additionally activates the human 5-HT$_7$ receptor and the 5-HT$_{2B}$ agonist additionally activates the human 5-HT$_2$ receptor at least ten-fold more than the extent to which each agonist activates each of the human 5-HT$_{1B}$, 5-HT$_{1D}$, 5-HT$_{1E}$, 5-HT$_{1F}$, 5-HT$_{5A}$, and 5-HT$_{5B}$ receptors.

In addition, the invention provides a process for making a composition of matter which specifically binds to a human 5-HT$_7$ receptor which comprises identifying a chemical compound using any of the processes described herein for identifying a compound which binds to and/or activates or inhibits activation of a human 5-HT$_7$ receptor and then synthesizing the chemical compound or a novel structural or functional analog or homolog thereof.

This invention further provides a process for preparing a pharmaceutical composition which comprises admixing a pharmaceutically acceptable carrier and a pharmaceutically acceptable amount of a chemical compound identified by any of the processes described herein for identifying a compound which binds to and/or activates or inhibits activation of a human 5-HT$_7$ receptor or a novel structural or functional analog or homolog thereof.

The invention also provides a process for making a composition of matter which specifically binds to human 5-HT$_7$ and 5-HT$_{2B}$ receptors which comprises identifying a chemical compound using any of the processes described herein for identifying a compound which binds to and /or activates or inhibits activation of human 5-HT$_7$ and 5-HT$_{2B}$ receptors and then synthesizing the chemical compound or a novel structural or functional analog or homolog thereof.

This invention further provides a process for preparing a pharmaceutical composition which comprises admixing a pharmaceutically acceptable carrier and a pharmaceutically acceptable amount of a chemical compound identified by any of the processes described herein for identifying a compound which binds to and/or activates or inhibits activation of human 5-HT$_7$ and 5-HT$_{2B}$ receptors or a novel structural or functional analog or homolog thereof.

BRIEF DESCRIPTION OF THE FIGURES

A more complete understanding of the invention and many of its advantages will become apparent by reference to the detailed description which follows when considered in conjunction with the accompanying figures, wherein:

FIG. 1

Southern blot from a rat urinary bladder showing the presence of mRNA for the 5-HT$_7$ receptor. +RT: lanes from samples treated by reverse transcriptase; H$_2$O: negative control; P: positive control; −RT: lanes from samples not treated by reverse transcriptase. See text for further explanation.

FIG. 2

Plot showing the correlation of antagonist affinities (pK$_B$ values) determined for a variety of antagonist ligands from functional studies of electrically stimulated rat bladder (abscissa) versus pK$_7$ values determined from radioligand binding studies using cloned human 5-HT$_{2B}$ receptors (ordinate). The correlation indicates that the 5-HT$_{2B}$ receptor mediates the contraction of the rat urinary bladder (the second phase of the concentration-effect curve to 5-CT).

FIG. 3

Plot showing the correlation of antagonist affinities (pK$_B$ values) determined for a variety of antagonist ligands from functional studies of electrically stimulated rat bladder (abscissa) versus pK$_1$ values determined from radioligand binding studies using cloned human 5-HT$_7$ receptors (ordinate). The correlation indicates that the 5-HT$_7$ receptor mediates the contraction of the rat urinary bladder (the first phase of the concentration-effect curve to 5-CT).

DETAILED DESCRIPTION OF THE INVENTION

The following definitions are presented as an aid in understanding this invention.

Receptor Activation describes the process by which the binding of a compound to the receptor when it is on the surface of a cell leads to a metabolic response within the cell. Such metabolic responses include, but are not limited to, activation of adenylate cyclase, activation of guanylate cyclase, hydrolysis of inositol phospholipids, movement of ions across the cell membrane, or contraction in a tissue in the cells of which the receptor is expressed.

Potency means the concentration of an agonist which elicits half of its own maximum activation (expressed as $EC_{50}$ or the negative log of the $EC_{50}$, i.e., $pEC_{50}$).

Intrinsic Activity means the magnitude of the maximum activation in a cell or tissue which a particular agonist is capable of eliciting, relative to the maximum activation elicited by a reference full agonist and expressed as values ranging between unity for full agonists (e.g., serotonin in the case of 5-HT-receptors) and zero for antagonists. Because intrinsic activity as originally defined by Ariens (1960) is recognized as being dependent upon the receptor system in which it is measured (Kenakin, 1987), intrinsic activity as referred to in this document is based upon measurements made using the cloned human 5-HT receptor systems described below.

Selectivity of Receptor Activation refers to the ability of an agonist to selectively activate one receptor relative to another receptor. Such selectivity may be reflect either (a) the agonist's ability to activate one receptor at a much lower concentration than required to activate another receptor (i.e., a potency difference) or (b) the agonist's ability to activate one receptor to a much greater degree than another receptor, independent of concentration, (i.e., an intrinsic activity difference) or (c) a combination of both.

Therefore, statements of the form "activates the $5-HT_7$ receptor ten-fold more than it activates one of the following (receptors)" mean and include any such difference whether it is by virtue of a difference in potency, or a difference in intrinsic activity, or both.

Having due regard to the preceding definitions, the present invention provides a method of treating urinary incontinence in a subject which comprises administering to the subject a therapeutically effective amount of a $5-HT_7$ antagonist which binds to the human $5-HT_7$ receptor with an affinity at least ten-fold higher than the affinity with which it binds to each of the human $5-HT_{1A}$, $5-HT_{2A}$, $5-HT_{2C}$, $5-HT_3$, $5-HT_4$, and $5-HT_6$ receptors.

Preferably, the aforementioned $5-HT_7$ antagonist additionally binds to the human $5-HT_7$ receptor with an affinity at least ten-fold higher than the affinity with which it binds to each of the human $5-HT_{1B}$, $5-HT_{1D}$, $5-HT_{1E}$, $5-HT_{1F}$, $5-HT_{5A}$, and $5-HT_{5B}$ receptors.

In certain embodiments the $5-HT_7$ antagonist also binds to the human $5-HT_7$ receptor with an affinity at least ten-fold higher than the affinity with which it binds to any human $\alpha_2$ adrenoceptor or any human $\beta$ adrenoceptor.

In other embodiments the $5-HT_7$ antagonist also binds to the human $5-HT_7$ receptor with an affinity at least ten-fold higher than the affinity with which it binds to the human histamine $H_1$ and $H_2$ receptors.

In still other embodiment the $5-HT_7$ antagonist also binds to the human $5-HT_7$ receptor with an affinity at least ten-fold higher than the affinity with which it binds to the human dopamine $D_1$, $D_2$, $D_3$, and $D_5$ receptors.

In still further embodiments the $5-HT_7$ antagonist also binds to the human $5-HT_7$ receptor with an affinity at least ten-fold higher than the affinity with which it binds to the human $\alpha_{1A}$ adrenoceptor and the human $\alpha_{1B}$ adrenoceptor.

Preferably, the $5-HT_7$ antagonist binds to the human $5-HT_7$ receptor with an affinity at least 50-fold higher than the affinity with which it binds to each of the human $5-HT_{1A}$, $5-HT_{2A}$, $5-HT_{2C}$, $5-HT_3$, $5-HT_4$, and $5-HT_6$ receptors.

More preferably, the $5-HT_7$ antagonist binds to the human $5-HT_7$ receptor with an affinity at least 100-fold higher than the affinity with which it binds to each of the human $5-HT_{1A}$, $5-HT_{2A}$, $5-HT_{2C}$, $5-HT_3$, $5-HT_4$, and $5-HT_6$ receptors.

Most preferably, the $5-HT_7$ antagonist binds to the human $5-HT_7$ receptor with an affinity at least 200-fold higher than the affinity with which it binds to each of the human $5-HT_{1A}$, $5-HT_{2A}$, $5-HT_{2C}$, $5-HT_3$, $5-HT_4$, and $5-HT_6$ receptors.

In an additional embodiment of the invention, the $5-HT_7$ antagonist is also a $5-HT_{2B}$ antagonist which binds to the human $5-HT_{2B}$ receptor with an affinity at least 10-fold higher than the affinity with which it binds to each of the human $5-HT_{1A}$, $5-HT_{2A}$, $5-HT_{2C}$, $5-HT_3$, $5-HT_4$, and $5-HT_6$ receptors.

Preferably, the $5-HT_7$ antagonist additionally binds to the human $5-HT_{2B}$ receptor with an affinity at least ten-fold higher than the affinity with which it binds to each of the human $5-HT_{1B}$, $5-HT_{1D}$, $5-HT_{1E}$, $5-HT_{1F}$, $5-HT_{5A}$, and $5-HT_{5B}$ receptors.

Preferably, the $5-HT_7$ antagonist binds to the human $5-HT_{2B}$ receptor with an affinity at least 50-fold higher than the affinity with which it binds to each of the human $5-HT_{1A}$, $5-HT_{2A}$, $5-HT_{2C}$, $5-HT_3$, $5-HT_4$, and $5-HT_6$ receptors.

More preferably, the $5-HT_7$ antagonist binds to the human $5-HT_{2B}$ receptor with an affinity at least 100-fold higher than the affinity with which it binds to each of the human $5-HT_{1A}$, $5-HT_{2A}$, $5-HT_{2C}$, $5-HT_3$, $5-HT_4$, and $5-HT_6$ receptors.

Most preferably, the $5-HT_7$ antagonist binds to the human $5-HT_{2B}$ receptor with an affinity at least 200-fold higher than the affinity with which it binds to each of the human $5-HT_{1A}$, $5-HT_{2A}$, $5-HT_{2C}$, $5-HT_3$, $5-HT_4$, and $5-HT_6$ receptors.

In certain embodiments the $5-HT_7$ antagonist is a $5-HT_{2B}$ antagonist which binds to the human $5-HT_{2B}$ receptor with an affinity at least ten-fold higher than the affinity with which it binds to any human $\alpha_2$ adrenoceptor or any human $\beta$ adrenoceptor.

In other embodiments the $5-HT_7$ antagonist is a $5-HT_{2B}$ antagonist which binds to the human $5-HT_{2B}$ receptor with an affinity at least ten-fold higher than the affinity with which it binds to the human histamine $H_1$ and $H_2$ receptors.

In still other embodiments the $5-HT_7$ antagonist is a $5-HT_{2B}$ antagonist which binds to the human $5-HT_{2B}$ receptor with an affinity at least ten-fold higher than the affinity with which it binds to the human dopamine $D_1$, $D_2$, $D_3$, and $D_5$ receptors.

In still further embodiments the $5-HT_7$ antagonist is a $5-HT_{2B}$ antagonist which binds to the human $5-HT_{2B}$ receptor with an affinity at least ten-fold higher than the affinity with which it binds to the human $\alpha_{1A}$ adrenoceptor and the human $\alpha_{1B}$ adrenoceptor.

The invention further provides a method of inducing contraction of a urinary bladder which comprises contacting the urinary bladder with an effective contraction-inducing amount of a $5-HT_7$ agonist which activates the human $5-HT_7$ receptor at least ten-fold more than it activates each of the human $5-HT_{1A}$, $5-HT_{2A}$, $5-HT_{2C}$, $5-HT_3$, $5-HT_4$, and $5-HT_6$ receptors.

The invention also provides a method of treating urinary retention in a subject which comprises administering to the subject a therapeutically effective amount of a $5-HT_7$ agonist which activates the human $5-HT_7$ receptor at least ten-fold more than it activates each of the human $5-HT_{1A}$, $5-HT_{2A}$, $5-HT_{2C}$, $5-HT_3$, $5-HT_4$, and $5-HT_6$ receptors.

Preferably, the aforementioned $5-HT_7$ agonist additionally activates the human $5-HT_7$ receptor at least ten-fold more than it activates each of the human $5-HT_{1B}$, $5-HT_{1D}$, $5-HT_{1E}$, $5HT_{1F}$, $5-HT_{5A}$, and $5-HT_{5B}$ receptors.

In certain embodiments the $5-HT_7$ agonist also activates the human $5-HT_7$ receptor at least ten-fold more than it activates any human $\alpha_2$ adrenoceptor or any human $\beta$ adrenoceptor.

In other embodiments the 5-HT$_7$ agonist also activates the human 5-HT$_7$ receptor at least ten-fold more than it activates the human histamine H$_1$ and H$_2$ receptors.

In still other embodiments the 5-HT$_7$ agonist also activates the human 5-HT$_7$ receptor at least ten-fold more than it activates the human dopamine D$_1$, D$_2$, D$_3$, and D$_5$ receptors.

In still further embodiments 5-HT$_7$ agonist also activates the human 5-HT$_7$ receptor at least ten-fold more than it activates the human α$_{1A}$ adrenoceptor and the human α$_{1B}$ adrenoceptor.

Preferably, the 5-HT$_7$ agonist activates the human 5-HT$_7$ receptor at least 50-fold more than it activates each of the human 5-HT$_{1A}$, 5-HT$_{2A}$, 5-HT$_{2C}$, 5-HT$_3$, 5-HT$_4$, and 5-HT$_6$ receptors.

More preferably, 5-HT$_7$ agonist activates the human 5-HT$_7$ receptor at least 100-fold more than it activates each of the human 5-HT$_{1A}$, 5-HT$_{2A}$, 5-HT$_{2C}$, 5-HT$_3$, 5-HT$_4$, and 5-HT$_6$ receptors.

Most preferably, the 5-HT$_7$ agonist activates the human 5-HT$_7$ receptor at least 200-fold more than it activates each of the human 5-HT$_{1A}$, 5-HT$_{2A}$, 5-HT$_{2C}$, 5-HT$_3$, 5-HT$_4$, and 5-HT$_6$ receptors.

In an additional embodiment of the invention, the 5-HT$_7$ agonist is also a 5-HT$_{2B}$ agonist which activates the human 5-HT$_{2B}$ receptor at least ten-fold more than it activates each of the human 5-HT$_{1A}$, 5-HT$_{2A}$, 5-HT$_{2C}$, 5-HT$_3$, 5-HT$_4$, and 5-HT$_6$ receptors.

Preferably, the 5-HT$_7$ agonist additionally activates the human 5-HT$_{2B}$ receptor at least ten-fold more than it activates each of the human 5-HT$_{1B}$, 5-HT$_{1D}$, 5-HT$_{1E}$, 5-HT$_{1F}$, 5-HT$_{5A}$, and 5-HT$_{5B}$ receptors.

Preferably, the 5-HT$_7$ agonist activates the human 5-HT$_{2B}$ receptor at least 50-fold more than it activates each of the human 5-HT$_{1A}$, 5-HT$_{2A}$, 5-HT$_{2C}$, 5-HT$_3$, 5-HT$_4$, and 5-HT$_6$ receptors.

More preferably, the 5-HT$_7$ agonist activates the human 5-HT$_{2B}$ receptor at least 100-fold more than it activates each of the human 5-HT$_{1A}$, 5-HT$_{2A}$, 5-HT$_{2C}$, 5-HT$_3$, 5-HT$_4$, and 5-HT$_6$ receptors.

Most preferably, the 5-HT$_7$ agonist activates the human 5-HT$_{2B}$ receptor at least 200-fold more than it activates each of the human 5-HT$_{1A}$, 5-HT$_{2A}$, 5-HT$_{2C}$, 5-HT$_3$, 5-HT$_4$, and 5-HT$_6$ receptors.

In certain embodiments the 5-HT$_7$ agonist is a 5-HT$_{2B}$ agonist which activates the human 5-HT$_{2B}$ receptor at least ten-fold more than it activates any human α$_2$ adrenoceptor or any human β adrenoceptor.

In other embodiments the 5-HT$_7$ agonist is a 5-HT$_{2B}$ agonist which activates the human 5-HT$_{2B}$ receptor at least ten-fold more than it activates the human histamine H$_1$ and H$_2$ receptors.

In still other embodiments the 5-HT$_7$ agonist is a 5-HT$_{2B}$ agonist which activates the human 5-HT$_{2B}$ receptor at least ten-fold more than it activates the human dopamine D$_1$, D$_2$, D$_3$, and D$_5$ receptors.

In still further embodiments the 5-HT$_7$ agonist is a 5-HT$_{2B}$ agonist which activates the human 5-HT$_{2B}$ receptor at least ten-fold more than it activates the human α$_{1A}$ adrenoceptor and the human α$_{1B}$ adrenoceptor.

The invention further provides a method of treating urinary incontinence in a subject which comprises administering to the subject a therapeutically effective amount of an admixture of a 5-HT$_7$ antagonist and a 5-HT$_{2B}$ antagonist, wherein both the affinity with which the 5-HT$_7$ antagonist binds to the human 5-HT$_7$ receptor and the affinity with which the 5-HT$_{2B}$ antagonist binds to the human 5-HT$_{2B}$ receptor are at least ten-fold higher than the affinity with which each antagonist binds to each of the human 5-HT$_{1A}$, 5-HT$_{2A}$, 5-HT$_{2C}$, 5-HT$_3$, 5-HT$_4$, and 5-HT$_6$ receptors.

Preferably, the 5-HT$_7$ antagonist additionally binds to the human 5-HT$_7$ receptor and the 5-HT$_{2B}$ antagonist additionally binds to the human 5-HT$_{2B}$ receptor with an affinity at least ten-fold higher than the affinity with which each antagonist binds to each of the human 5-H$_{1B}$, 5-HT$_{1D}$, 5-HT$_{1E}$, 5-HT$_{1F}$, 5-HT$_{5A}$, and 5-HT$_{5B}$ receptors.

In certain embodiments at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least ten-fold higher than the affinity with which said antagonist binds to any human α$_2$ adrenoceptor or any human β adrenoceptor.

In other embodiments at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least ten-fold higher than the affinity with which said antagonist binds to the human histamine H$_1$ and H$_2$ receptors.

In still other embodiments at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least ten-fold higher than the affinity with which said antagonist binds to the human dopamine D$_1$, D$_2$, D$_3$, and D$_5$ receptors.

In still further embodiments at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least ten-fold higher than the affinity with which said antagonist binds to the human α$_{1A}$ adrenoceptor and the human α$_{1B}$ adrenoceptor.

Preferably, at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least 50-fold higher than the affinity with which said antagonist binds to each of the human 5-HT$_{1A}$, 5-HT$_{2A}$, 5-HT$_{2C}$, 5-HT$_3$, 5-HT$_4$, and 5-HT$_6$ receptors.

More preferably, at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least 100-fold higher than the affinity with which said antagonist binds to each of the human 5-HT$_{1A}$, 5-HT$_{2A}$, 5-HT$_{2C}$, 5-HT$_3$, 5-HT$_4$, and 5-HT$_6$ receptors.

Most preferably, at least one of the affinity with which the 5-HT$_7$ antagonist binds to the human 5-HT$_7$ receptor or the affinity with which the 5-HT$_{2B}$ antagonist binds to the human 5-HT$_{2B}$ receptor is at least 200-fold higher than the affinity with which said antagonist binds to each of the human 5-HT$_{1A}$, 5-HT$_{2A}$, 5-HT$_{2C}$, 5-HT$_3$, 5-HT$_4$, and 5-HT$_6$ receptors.

The invention also provides a method of treating urinary retention in a subject which comprises administering to the subject a therapeutically effective amount of an admixture of a 5-HT$_7$ agonist and a 5-HT$_{2B}$ agonist, wherein both the 5-HT$_7$ agonist activates the human 5-HT$_7$ receptor and the 5-HT$_{2B}$ agonist activates the human 5-HT$_{2B}$ receptor at least ten-fold more than the extent to which each agonist activates each of the human 5-HT$_{1A}$, 5-HT$_{2A}$, 5-HT$_{2C}$, 5-HT$_3$, 5-HT$_4$, and 5-HT$_6$ receptors.

Preferably, the 5-HT$_7$ agonist additionally activates the human 5-HT$_7$ receptor and the 5-HT$_{2B}$ agonist additionally activates the human 5-HT$_{2B}$ receptor at least ten-fold more than the extent to which each agonist activates each of the human 5-HT$_{1B}$, 5-HT$_{1D}$, 5-HT$_{1E}$, 5-HT$_{1F}$, 5-HT$_{5A}$, and 5-HT$_{5B}$ receptors.

In certain embodiments at least one of the extent to which the 5-HT$_7$ agonist activates the human 5-HT$_7$ receptor or the extent to which the 5-HT$_{2B}$ agonist activates the human 5-HT$_{2B}$ receptor is at least ten-fold more than the extent to which said agonist activates any human $\alpha_2$ adrenoceptor or any human $\beta$ adrenoceptor.

In other embodiments at least one of the extent to which the 5-HT$_7$ agonist activates the human 5-HT$_7$ receptor or the extent to which the 5-HT$_{2B}$ agonist activates the human 5-HT$_{2B}$ receptor is at least ten-fold more than the extent to which said agonist activates the human histamine H$_1$ and H$_2$ receptors.

In still other embodiments at least one of the extent to which the 5-HT$_7$ agonist activates the human 5-HT$_7$ receptor or the extent to which the 5-HT$_{2B}$ agonist activates the human 5-HT$_{2B}$ receptor is at least ten-fold more than the extent to which said agonist activates the human dopamine D$_1$, D$_2$, D$_3$, and D$_5$ receptors.

In still further embodiments at least one of the extent to which the 5-HT$_7$ agonist activates the human 5-HT$_7$ receptor or the extent to which the 5-HT$_{2B}$ agonist activates the human 5-HT$_{2B}$ receptor is at least ten-fold more than the extent to which said agonist activates the human $\alpha_{1A}$ adrenoceptor and the human $\alpha_{1B}$ adrenoceptor.

Preferably, at least one of the extent to which the 5-HT$_7$ agonist activates the human 5-HT$_7$ receptor or the extent to which the 5-HT$_{2B}$ agonist activates the human 5-HT$_{2B}$ receptor is at least 50-fold more than the extent to which said agonist activates each of the human 5-HT$_{1A}$, 5-HT$_{2A}$, 5-HT$_{2C}$, 5-HT$_3$, 5-HT$_4$, and 5-HT$_6$ receptors.

More preferably, at least one of the extent to which the 5-HT$_7$ agonist activates the human 5-HT$_7$ receptor or the extent to which the 5-HT$_{2B}$ agonist activates the human 5-HT$_{2B}$ receptor is at least 100-fold more than the extent to which said agonist activates each of the human 5-HT$_{1A}$, 5-HT$_{2A}$, 5-HT$_{2C}$, 5-HT$_3$, 5-HT$_4$, and 5-HT$_6$ receptors.

Most preferably, at least one of the extent to which the 5-HT$_7$ agonist activates the human 5-HT$_7$ receptor or the extent to which the 5-HT$_{2B}$ agonist activates the human 5-HT$_{2B}$ receptor is at least 200-fold more than the extent to which said agonist activates each of the human 5-HT$_{1A}$, 5-HT$_{2A}$, 5-HT$_{2C}$, 5-HT$_3$, 5-HT$_4$, and 5-HT$_6$ receptors.

This invention provides a process for making a composition of matter which specifically binds to a human 5-HT$_7$ receptor which comprises identifying a chemical compound using any of the processes described herein for identifying a compound which binds to and/or activates or inhibits activation of a human 5-HT$_7$ receptor and then synthesizing the chemical compound or a novel structural or functional analog or homolog thereof.

This invention further provides a process for preparing a pharmaceutical composition which comprises admixing a pharmaceutically acceptable carrier and a pharmaceutically acceptable amount of a chemical compound identified by any of the processes described herein for identifying a compound which binds to and/or activates or inhibits activation of a human 5-HT$_7$ receptor or a novel structural or functional analog or homolog thereof.

The invention also provides a process for making a composition of matter which specifically binds to human 5-HT$_7$ and 5-HT$_{2B}$ receptors which comprises identifying a chemical compound using any of the processes described herein for identifying a compound which binds to and/or activates or inhibits activation of human 5-HT$_7$ and 5-HT$_{2B}$ receptors and then synthesizing the chemical compound or a novel structural or functional analog or homolog thereof.

This invention further provides a process for preparing a pharmaceutical composition which comprises admixing a pharmaceutically acceptable carrier and a pharmaceutically acceptable amount of a chemical compound identified by any of the processes described herein for identifying a compound which binds to and/or activates or inhibits activation of human 5-HT$_7$ and 5-HT$_{2B}$ receptors or a novel structural or functional analog or homolog thereof.

The binding and functional properties of compounds at the different human receptors were determined in vitro using cultured cell lines that selectively express the receptor of interest. These cell lines were prepared by transfecting the cloned cDNA or cloned genomic DNA or constructs containing both genomic DNA and cDNA encoding the human 5-HT$_7$ or 5-HT$_{2B}$ receptor as further described in detail in the Examples herein below.

In connection with this invention, a number of cloned human receptors discussed herein, either as plasmids or as stably transfected cell lines, have been made pursuant to, and in satisfaction of, the Budapest Treaty on the International Recognition of the Deposit of Microorganisms for the Purpose of Patent Procedure, and are made with the American Type Culture Collection, 10801 University Blvd., Manassas, Va. 20110-2209. Specifically, these deposits have been accorded ATCC Accession Numbers as follows:

| ATCC Deposits: | | | |
| --- | --- | --- | --- |
| Designation | Receptor | ATCC Accession No. | Date of Deposit |
| Cell lines: | | | |
| L-$\alpha_{1A}$ | human $\alpha_{1A}$ | CRL 11138 | 09/25/1992 |
| L-$\alpha_{1B}$ | human $\alpha_{1B}$ | CRL 11139 | 09/25/1992 |
| L-$\alpha_{1C}$ | human $\alpha_{1C}$ | CRL 11140 | 09/25/1992 |
| L-$\alpha_{2A}$ | human $\alpha_{2A}$ | CRL 11180 | 11/6/1992 |
| L-NGC-$\alpha_{2B}$ | human $\alpha_{2B}$ | CRL 10275 | 10/25/1989 |
| Y-a2B-2 | human $\alpha_{2B}$ | CRL 11888 | 05/11/1995 |
| L-$\alpha_{2C}$ | human $\alpha_{2C}$ | CRL 11181 | 11/6/1992 |
| Ltk-8-30-84 | human 5-HT$_{1D1}$ | CRL 10421 | 04/17/1990 |
| Ltk-11 | human 5-HT$_{1D2}$ | CRL 10422 | 04/17/1990 |
| 5HT$_{1E}$-7 | human 5-HT$_{1E}$ | CRL 10913 | 11/6/1991 |
| L-5-HT$_{1F}$ | human 5-HT$_{1F}$ | CRL 10957 | 12/27/1991 |
| L-5HT-4B* | human 5-HT$_{4B}$ | CRL 11166 | 10/20/1992 |
| 5HT1A-3 | human 5-HT$_{1A}$ | CRL 11889 | 05/11/1995 |
| L-NGC-5HT$_2$ | human 5-HT$_2$ | CRL 10287 | 10/31/1989 |
| Plasmids: | | | |
| pcEXV-D2 | human D2 | 75344 | 11/6/1992 |
| pcEXV-H2 | human H2 | 75345 | 11/6/1992 |
| pcEXV-H1 | human H1 | 75346 | 11/6/1992 |

*The "5-HT$_{4B}$" receptor was renamed the "5-HT$_7$" receptor by the Serotonin Receptor Nomenclature Committee of the IUPHAR.

The data shown in the accompanying Tables and Figures indicate that it is both the 5-HT$_7$ and 5-HT$_{2B}$ serotonin receptors which are responsible for augmenting the electrical stimulation-induced contractions of the rat urinary bladder. This in vitro property is recognized in the art as correlating with efficacy in treating urinary incontinence in vivo, providing that a similar expression of the 5-HT$_7$ and/or 5-HT$_{2B}$ receptors is present in pathological conditions in the human bladder.

The present invention therefore provides a method of treating urinary disorders, which comprises administering to a subject a therapeutically effective amount of any of the 5-HT$_7$ receptor agonists or antagonists defined herein or a therapeutically effective amount of any of the agonists or antagonists that act at both 5-HT$_7$ and 5-HT$_{2B}$ receptors as defined herein. The drug may be administered to a patient afflicted with a urinary disorder by any conventional route of administration, including, but not limited to, intravenous, intramuscular, oral, subcutaneous, intratumoral, intradermal, and parenteral. In one embodiment, the therapeutically effective amount is between about 0.001 mg and about 10.0 mg per kg of subject body weight.

The method of treating urinary disorders disclosed in the present invention may also be carried out using a pharmaceutical composition comprising a therapeutically effective amount of any of the 5-HT$_7$ receptor agonists or antagonists as defined herein and a pharmaceutically acceptable carrier, or a therapeutically effective amount of an agonist or antagonist that acts at both the 5-HT$_7$ and 5-HT$_{2B}$ receptors as defined herein and a pharmaceutically acceptable carrier. In one embodiment, the composition may contain between about 0.05 mg and about 500 mg of a 5-HT$_7$ receptor agonist or antagonist. In another embodiment, the composition may contain between about 0.05 mg and about 500 mg of an agonist or antagonist that acts at both 5-HT$_7$ and 5-HT$_{2B}$ receptors.

The composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The drug may also be formulated as a transdermal patch.

Optimal dosages to be administered may be readily determined by those skilled in the art, and will vary with the particular 5-HT$_7$ receptor agonist or antagonist in use or the particular 5-HT$_7$ and 5-HT$_{2B}$ receptor agonist or antagonist in use, the strength of the preparation, the mode of administration, and the advancement of the disease condition. Additional factors depending on the particular patient being treated will result in a need to adjust dosages, including patient age, weight, diet, and time of administration.

The term "therapeutically effective amount" as used herein refers to any amount of a compound which, when administered to a subject suffering from a disease against which the compound is effective, causes reduction, remission, or regression of the disease.

The term "subject," as used herein refers to an animal, preferably a mammal, most preferably a human, who has been the object of treatment, observation or experiment.

Cell Transfections

Transient transfections of COS-7 cells with various plasmids were performed using the DEAE-Dextran method, which is well-known to those skilled in the art. Briefly, a plasmid comprising an expression vector for the receptor of interest was added to monolayers of COS-7 cells bathed in a DEAE-Dextran solution. In order to enhance the efficiency of transfection, dimethyl sulfoxide was typically also added, according to the method of Lopata (Lopata, et al., 1984). Cells were then grown under controlled conditions and used in experiments after about 72 hours.

Stable cell lines were obtained using means which are well-known in the art. For example, a suitable host cell was typically cotransfected, using the calcium phosphate technique, with a plasmid comprising an expression vector for the receptor of interest and a plasmid comprising a gene which allows selection of successfully transfected cells. Cells were then grown in a controlled environment, and selected for expression of the receptor of interest. By continuing to grow and select cells, stable cell lines were obtained expressing the receptors described and used herein.

Binding Assays

The binding of a test compound to a receptor of interest was generally evaluated by competitive binding assays using membrane preparations derived from cells which expressed the receptor. First, conditions were determined which allowed measurement of the specific binding of a compound known to bind to the receptor. Then, the binding of the known compound to the receptor in membrane preparations was evaluated in the presence of several different concentrations of the test compound. Binding of the test compound to the receptor resulted in a reduction in the amount of the known compound which was bound to the receptor. A test compound having a high affinity for the receptor of interest would displace a given fraction of the bound known compound at a concentration lower than the concentration which would be required if the test compound had a low affinity for the receptor of interest.

This invention will be better understood from the Experimental Details which follow. However, one skilled in the art will readily appreciate that the specific methods and results discussed are merely illustrative of the invention as described more fully in the claims which follow thereafter.

Experimental Details

The following Experimental Details are set forth to aid in an understanding of the invention, and are not intended, and should not be construed, to limit in any way the invention set forth in the claims which follow thereafter.

Macrolocalization (PCR/Tissue Transcriptional Expression Studies). Rat bladder tissues were homogenized and total RNA extracted using guanidine isothiocyanate/CsCl cushion method as previously described (Kingston, 1987). cDNA was prepared from 5 µg of total RNA with random hexanucleotide primers (500 pmoles) using Superscript reverse transcriptase (BRL) in 50 mM Tris-HCl, pH 8.3, buffer containing 40 U RNAsin, 2.5 mM MgCl$_2$, 50 mM KCl and 1 mM dNTPs at 42° C. for 1 hour. RNase H (2U) was added, incubated for 20 min at 37° C., followed by heating at 95° C. for 5 min, and chilled on ice. An aliquot of the first strand cDNA was diluted (1:5) in a 50 µl PCR reaction mixture (200 µM dNTPs final concentration) containing 1.25 U of Taq polymerase in the buffer supplied by the manufacturer (Cetus Corp.), and 1 µM of primers in a PCR protocol (the 5' and 3' oligos were the same as used for screening cDNA libraries; see below). The PCR amplification reaction was carried out by first a 5 min incubation at 95° C. followed by 30 rounds of the following cycle: 2 min at 94° C., 2 min at 68° C., 3 min at 72° C., followed at the end by 10 min incubation at 72° C. In order to control for the amplification of DNA (carried over during the RNA extraction), control PCR reactions were run in parallel with RNA diluted in the same manner as the cDNA sample. The PCR products were run on a 1.5% agarose gel and transferred to charged nylon membrane (ZetaProbe, BioRad). Filters were hybridized with [$\gamma$-$^{32}$P]ATP-end-labeled internal probe to the PCR primers (this oligo was the same as used for screening the initial human fetal brain cDNA library; see below), washed under high stringency (50° C.), and exposed at −70° C. to Kodak XAR film in the presence of an intensifying screen. Antisense and sense oligonucleotides (45mers) to the rat 5-HT$_7$ mRNA were synthesized on a Cyclone Plus DNA Synthesizer (Milligen/Biosearch). Probes were 3'-end labeled with $^{35}$S-dATP (1200 Ci/mmol, New England Nuclear, Boston, Mass.) to a specific activity of 10$^9$ dpm/$\mu$g using terminal deoxynucleotidyl transferase (Boehringer Mannheim; Indianapolis, Ind.). The radiolabeled probes were purified on Biospin 6 chromatography columns (Bio-Rad; Richmond, Calif.), and diluted in hybridization buffer to a concentration of 1.5×10$^4$ cpm/$\mu$l. The hybridization buffer consisted of 5% formamide, 4×sodium citrate buffer (SSC; 1×=0.15 M NaCl and 0.015 M sodium citrate), 1×Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate.

Rat Tissue Distribution of RNA Coding for the 5-HT$_7$ Receptor Gene. Total RNA isolated from rat bladder tissue was converted to single-stranded cDNA by random-priming with reverse transcriptase. cDNA was amplified by PCR using rat 5-HT$_7$ receptor gene specific PCR primers. PCR products were run on a 1.5% agarose gel, blotted on nylon membranes and hybridized to internal gene-specific oligonucleotides. Following hybridization, blots were washed under high stringency. Positive controls consisted of gene-specific recombinant plasmid; dH$_2$O served as a negative control, containing all reagents except template cDNA, RNA or plasmid. PCR amplification and Southern blotting of samples not treated with reverse transcriptase were negative.

Figure 1:
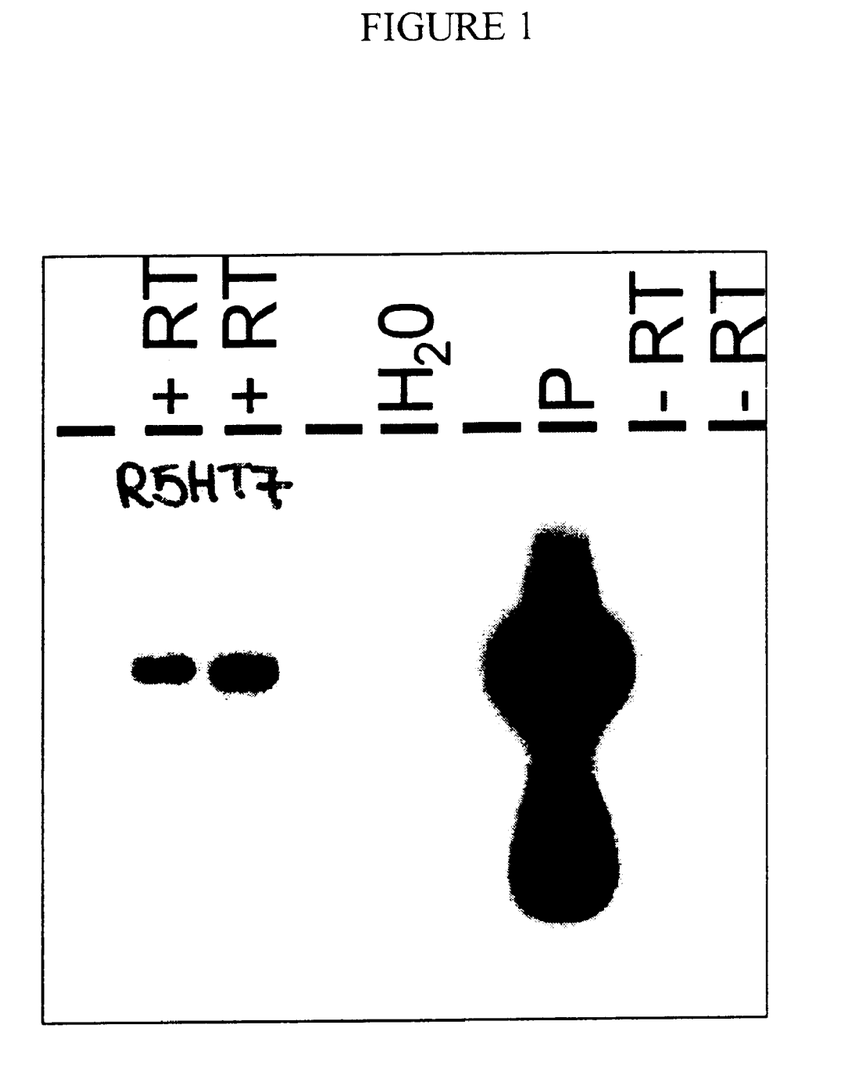

The expression of rat 5-HT$_7$ transcripts was analyzed by amplification of cDNA derived from RNA isolated from rat bladder (reverse transcription PCR or RT-PCR). The mRNA encoding the rat 5-HT$_7$ receptor was found to be expressed at high levels in the rat bladder (FIG. 1), similar to what we described previously for expression of the human 5-HT$_7$ receptor in the human bladder (Bard et al., DNA Encoding a Human Serotonin Receptor (5-HT$_{4B}$) And Uses Thereof, U.S. patent application Ser. No. 08/281,526, now U.S. Pat. No. 6,083,749, issued Jul. 4, 2000).

5-HT$_7$ compounds. 5-HT$_7$ antagonists are well-known in the art. See, for example, Kikuchi, et al., 1999; Forbes, et al., 1998; Forbes, et al, 1997; Forbes, 1997; Godel, et al., 1999; May, et al., 1999; and Koyama, et al., 1998.

5-HT$_{2B}$ compounds. 5-HT$_{2B}$ antagonists are well-known in the art. See, for example, Baxter, 1996; Baxter, et al., 1995; Forbes, et al., 1995; Bonhaus, et al., 1999; Audia, et al., 1997a; Audia, et al., 1997b; Audia, et al., 1997c; Audia, et al., 1995; and Audia, et al., 1997d. 5-HT$_{2B}$ agonists are well-known in the art. See, for example, Baxter, 1996; Kennett, et al., 1997; and Kennett, et al., 1996.

EXAMPLES

The binding and functional properties of compounds at the different human receptors were determined in vitro using cultured cell lines that selectively express the receptor of interest. These cell lines were prepared by transfecting the cloned cDNA or cloned genomic DNA or constructs containing both genomic DNA and cDNA encoding the human alpha-adrenergic receptors as follows:

Human $\alpha_{1A}$ Adrenergic Receptor. The entire coding region of $\alpha_{1A}$ (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequences were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid $\alpha_{1A}$/EXJ (expression vector containing the $\alpha_{1A}$ receptor gene) and the plasmid pGCcos3neo (plasmid containing the aminoglycoside transferase gene) into LM(tk−), CHO, and NIH3T3 cells, using calcium phosphate technique. The cells were grown, in a controlled environment (37° C., 5% CO$_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 $\mu$/ml streptomycin sulfate. Stable clones were then selected for resistance to the antibiotic G-418 (1 mg/ml) and membranes were harvested and assayed for their ability to bind [$^3$H]prazosin as described below (see "Radioligand Binding assays").

Human $\alpha_{1B}$ Adrenergic Receptor. The entire coding region of $\alpha_{1B}$ (1563 bp), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from ZapII into the expression vector. Stable cell lines were selected as described above.

Human $\alpha_{1C}$ Adrenergic Receptor. The entire coding region of $\alpha_{1C}$ (1401 bp), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays

Human $\alpha_1$-Adrenoceptors. Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM MgCl$_2$, and 0.1% ascorbic acid at pH 7.5. Binding of the $\alpha_1$ antagonist [$^3$H]prazosin (0.5 nM, specific activity: about 76.2 Ci/mmol) to membrane preparations of LM(tk−) cells was done in a final volume of 0.25 ml and incubated at 37° C. for 20 min. Nonspecific binding was defined as that binding which remained in the presence of 10 $\mu$M phentolamine (a concentration at least 100-fold greater than the affinity of phentolamine at any human $\alpha$-adrenoceptors).

The reaction was stopped by filtration through GF/B filters using a cell harvester. Equilibrium competition binding assays, routinely consisting of 7 different concentrations of the tested compounds, were analyzed using a non-linear regression curve-fitting computer program to obtain $IC_{50}$ values. The $IC_{50}$ values were converted to affinity constants (pK1) by the method of Cheng and Prusoff (1973).

Human $\alpha_2$-Adrenoceptors. To determine the affinity of compounds at the 2 receptors, LM(tk−) cell lines stably transfected with the genes encoding the $\alpha_{2A}$, $\alpha_{2B}$ and $\alpha_{2C}$ receptors were used. Cell lysates were prepared as described above (see Radioligand Binding Assays), and suspended in 25 mM glycylglycine buffer (pH 7.6 at room temperature). Equilibrium competition binding assays were performed using [$^3$H]rauwolscine (0.5 nM), and nonspecific binding was determined by incubation with 10 μM phentolamine. The bound radioligand was separated by filtration through GF/B filters using a cell harvester.

Human Histamine $H_1$ Receptor. The coding sequence of the human histamine $H_1$ receptor, homologous to the bovine $H_1$ receptor, was obtained from a human hippocampal cDNA library, and was cloned into the eukaryotic expression vector pCEXV-3. The plasmid DNA for the $H_1$ receptor is designated pcEXV-H1, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min. at 4° C. The pellet was suspended in 37.8 mM $NaHPO_4$, 12.2 mM $KH_2PO_4$, pH 7.5. The binding of the histamine H1 antagonist [$^3$H]mepyramine (1 nM, specific activity: about 24.8 Ci/mM) was done in a final volume of 0.25 ml and incubated at room temperature for 60 min. Nonspecific binding was determined in the presence of 10 μM mepyramine. The bound radioligand was separated by filtration through GF/B filters using a cell harvester.

Human Histamine $H_2$ Receptor. The coding sequence of the human $H_2$ receptor was obtained from a human placenta genomic library, and cloned into the cloning site of PCEXV-3 eukaryotic expression vector. The plasmid DNA for the $H_2$ receptor is designated pcEXV-H2, and was deposited on Nov. 6, 1992 under ATCC Accession No. 75345. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4 C., and the supernatant was centrifuged at 30,000×g for 20 min at 4° C. The pellet was suspended in 37.8 mM $NaHPO_4$, 12.2 mM $K_2PO_4$, pH 7.5. The binding of the histamine $H_2$ antagonist [$^3$H]tiotidine (5 nM, specific activity: about 70 Ci/mM) was done in a final volume of 0.25 ml and incubated at room temperature for 60 min. Nonspecific binding was determined in the presence of 10 μM histamine. The bound radioligand was separated by filtration through GF/B filters using a cell harvester.

Human Serotonin Receptors. $5\text{-}HT_{1D\alpha}$, $5\text{-}HT_{1D\beta}$, $5\text{-}HT_{1E}$, $5\text{-}HT_{1F}$, and $5\text{-}HT_7$ Receptors: The cell lysates of LM(tk−) clonal cell line stably transfected with the genes encoding each of these 5-HT receptor-subtypes were prepared as described above. The cell line for the $5\text{-}HT_{1D\alpha}$ receptor, designated as Ltk-8-30-84, was deposited on Apr. 17, 1990, and accorded ATCC Accession No. CRL 10421. The cell for the $5\text{-}HT_{1D\beta}$ receptor, designated as Ltk-11, was deposited on Apr. 17, 1990, and accorded ATCC Accession No. CRL 10422. The cell line for the $5\text{-}HT_{1E}$ receptor, designated 5-HT1E-7, was deposited on Nov. 6, 1991, and accorded ATCC Accession No. CRL 10913. The cell line for the $5\text{-}HT_{1F}$ receptor, designated L-5-$HT_{1F}$, was deposited on Dec. 27, 1991, and accorded ATCC Accession No. ATCC 10957. The cell line for the $5\text{-}HT_7$ receptor, designated as L-5HT-4B, was deposited on Oct. 20, 1992, and accorded ATCC Accession No. CRL 11166. These preparations were suspended in 50 mM Tris-HCl buffer (pH 7.4 at 37° C.) containing 10 mM $MgCl_2$, 0.2 mM EDTA, 10 M pargyline, and 0.1% ascorbate. The affinities of compounds were determined in equilibrium competition binding assays by incubation for 30 minutes at 37° C. in the presence of 5 nM [$^3$H]serotonin. Nonspecific binding was determined in the presence of 10 μM serotonin. The bound radioligand was separated by filtration through GF/B filters using a cell harvester.

Human $5\text{-}HT_{2A}$ Receptor. The coding sequence of the human $5\text{-}HT_{2A}$ receptor was obtained from a human brain cortex cDNA library, and cloned into the cloning site of pCEXV-3 eukaryotic expression vector. This construct was transfected into COS-7 cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-5HT2, and was accorded ATCC Accession No. CRL 10287. The cell lysates were centrifuged at 1000 rpm for 5 minutes at 4° C., and the supernatant was centrifuged at 30,000×g for 20 minutes at 4° C. The pellet was suspended in 50 mM Tris-HCl buffer (pH 7.7 at room temperature) containing 10 mM $MgSO_4$, 0.5 mM EDTA, and 0.1% ascorbate. The affinity of compounds at $5\text{-}HT_{2A}$ receptors were determined in equilibrium competition binding assays using [$^3$H]ketanserin (1 nM). Nonspecific binding was defined by the addition of 10 μM mianserin. The bound radioligand was separated by filtration through GF/B filters using a cell harvester.

$5\text{-}HT_{1A}$ Receptor. The cell line for the $5\text{-}HT_{1A}$ receptor, designated as 5HT1A-3, was deposited on May 11, 1995, and accorded ATCC Accession No. CRL 11889. The cDNA corresponding to the $5\text{-}HT_{1A}$ receptor open reading frames and variable non-coding 5'- and 3'-regions, was cloned into the eukaryotic expression vector pCEXV-3. These constructs were transfected transiently into COS-7 cells by the DEAE-dextran method, and harvested after 72 hours. Radioligand binding assays were performed as described above for the $5\text{-}HT_2$ receptor, except that $^3$H-8-OH-DPAT was used as the radioligand and nonspecific binding was determined by the addition of 10 μM mianserin.

Human Dopamine $D_2$ Receptors. The affinity of compounds at the $D_2$ receptor were determined using membrane preparations from COS-7 cells transfected with the gene encoding the human $D_2$ receptor. The coding region for the human $D_2$ receptor was obtained from a human striatum cDNA library, and cloned into the cloning site of PCDNA 1 eukariotic expression vector. The plasmid DNA for the $D_2$ receptor is designated pcEXV-D2, and was deposited on Nov. 6, 1992 under ATCC Accession No. ATC 75344. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 minutes at 4° C., and the supernatant was centrifuged at 30,000×g for 20 minutes at 4° C. The pellet was suspended in 50 mM Tris-HCl (pH 7.4) containing 1 mM EDTA, 5 mM KCl, 1.5 mM $CaCl_2$, 4 mM $MgCl_2$, and 0.1% ascorbic acid. The cell lysates were incubated with [$^3$H]spiperone (2 nM), using 10 μM (+)butaclamol to determine nonspecific binding.

Other Dopamine receptors were prepared by known methods: (D$_1$: Dearry et al., 1990, deposited with the European Molecular Biological Laboratory (EMBL) Genbank as X55760; D$_3$: Sokoloff et al.,1990, deposited with the European Molecular Biological Laboratory (EMBL) Genbank as X53944; D$_5$: Sunahara et al. 1991, deposited with EMBL Genbank as X58454-HU HD 5DR).

Functional Assays in Cloned Receptors

5-HT$_7$-Receptor-Mediated Stimulation of Adenylate Cyclase

Transiently transfected Cos-7 cells, untransfected Cos-7 cells and stably transfected LM(tk-) cells were tested for the ability of 5-HT to modify intracellular cAMP levels. Both the 5-HT-mediated inhibition and stimulation of cAMP levels were evaluated in these three intact cell preparations. Intracellular cAMP formation was measured by radioimmunoassay (cAMP Radioimmunoassay kit, Advanced Magnetics, Cambridge, Mass.) using methodology outlined by Zgombick et al. (1991). Radioactivity was quantified using a Packard COBRA Auto Gamma Counter (equipped with data reduction software).

Isolated Tissue Assays

Protocol for the Identification of 5-HT$_7$ and 5-HT$_{2B}$ Receptor Subtype in Urinary Bladder from Functional Studies 5-HT receptors in the rat urinary bladder which, when activated by serotonin agonists, cause increases in the magnitude of nerve-mediated contractions, were identified and characterized pharmacologically using isolated strips of rat bladder.

Methods

Preparation of Urinary Bladder Strips

Urinary bladders were isolated from female CD rats (Charles Rivers, 250–300 g). The bladder base (lower third) was removed and the detrusor region was opened into a flat sheet by cutting from the basal opening to the apex. This was cut into quadrants, each of which was attached on its lateral edges by two tissue clips and suspended in a 5ml tissue bath containing Krebs' solution (pH 7.4, 37° C.) of the following composition (mM): NaCl (118), KCl (4.9), NaHCO$_3$ (25), MgCl$_2$ (1.2), NaHPO$_4$ (1.0), CaCl$_2$ (2.5), glucose (11) and aerated continuously with 95% O$_2$/5% CO$_2$. Except in initial experiments, prazosin (0.1 μM), idazoxan (0.3 μM), and indomethacin (10 μM) were included routinely in the buffer to block α$_2$- and α$_2$-adrenoceptors and to prevent the formation of prostaglandins, respectively. After allowing 30 min for equilibration, bladder strips were placed under 1.0 g resting tension, readjusted 6 times over the next 30 min. For most experiments contractile responses were evoked by transmural electrical impulses delivered by Grass S-88 (Grass Instruments, City, Mass.) stimulators (single pulses, 0.1 Hz, 1 ms pulse width, 90V) through a pair of stainless steel electrodes. Contractions were measured using isometric force transducers (Radnotti Instruments, Monrovia, Calif.) and recorded using MacLab software (AD Instruments, Milford, Mass.).

Experimental Protocol and Concentration-effect Curves

Bladder strips, in Krebs' solution containing antagonist or vehicle, were stimulated at supramaximal voltage until contractions of consistent magnitude were obtained (ca. 30 min). During this period the Krebs' solution was exchanged at 15 min intervals. Cumulative concentration-effect curves were then constructed by administering 5-carboxamidotryptamine (5-CT) or other agonists in 0.5 log M increments. Responses are expressed as a percent of control, and represent agonist-evoked increases in the magnitude of the electrically evoked contractions relative to that in the absence of agonist ("control", taken as 100%). Preliminary experiments indicated that a second concentration-effect curve in a single tissue varied non-systematically in both potency (EC$_{50}$) and the maximum response relative to the first curve. Therefore, only a single agonist concentration-effect curve was constructed in each tissue.

pK$_5$ Estimates, Curve Fitting and Statistics

Concentration-effect curves were fitted (Kaleidagraph, Synergy Software, PCS Inc., Reading Pa.) to 1-site or 2-site models of agonism as represented by the following equations:

(1-site): Effect=$E_{max}[A]^n/[A]^n+EC_{50}^n$;

(2-site): Effect=$(E_{max}{}^a[A]/[A]+EC_{50}{}^a+(E_{max}{}^b[A]/[A]+EC_{50}{}^b)$, where E$_{max}$ represents the maximum effect of the agonist, [A] is the agonist molar concentration, EC$_{50}$ is the concentration of agonist eliciting half its maximum effect, n is the slope factor, and the italicized superscripts (a and b) denote values for the first and second phase of the biphasic curve. Antagonist pK$_B$ values were determined using the formula described by Furchgott (1972): pK$_B$=log (agonist concentration ratio −1/antagonist concentration [M]). In some instances, pK$_B$ values were determined according to the method of Arunlakshana and Schild (1959), in which the slope of the Schild plot was constrained to unity. Concentration ratios for Schild analyses were calculated from mean EC$_{50}$ values for the agonist in the absence and presence of the antagonist in experiments from n different animals.

Drugs

The drugs used were obtained from the following sources: 5-hydroxytryptamine creatinine sulfate, (−)-pindolol, mesulergine HCl, spiperone HCl, ketanserin tartrate, rauwolscine, 1-(1-naphthyl)piperazine HCl, tropisetron, prazosin HCl, idazoxan HCl, indomethacin and rauwolscine HCl (RBI, Natick, Mass.); methiothepin maleate (BioMol, Plymouth Meeting, Pa.); 5-carboxamidotryptamine and α-methyl-5-hydroxytryptamine (Tocris Cookson, Ballwin, Mo.); 5-fluorotryptamine (Sigma, St. Louis, Mo.). LY215840 was a gift from Dr. D. L. Nelson (Eli Lilly and Company, Indianapolis, Ind.). All drugs were dissolved in deionized water.

Results

5-HT produced marked increases in the magnitude of electrically evoked contractions. The effect of 5-HT was sustained, showing no evidence of acute desensitization. The effect of 5-HT was mimicked by the indoleamines 5-MeOT, alpha-Me-5-HT, DP-5-CT and 5-CT. The subtype selective agonists BIMU-8 (5-HT$_4$-selective) and 8-OH-DPAT (5-HT$_{1A}$-selective) were inactive, suggesting that 5-HT$_4$ and 5-HT$_{1A}$ receptors were not involved. This conclusion was supported further by the failure of BIMU-8 and 8-OH-DPAT (10 μM) to modify the effects of 5-HT.

Concentration-effect curves to 5-HT, 5-MeOT and α-Me-5-HT were broad (slope factors 0.4 to 0.7) and resistant to competitive-like blockade by a variety of 5-HT receptor antagonists, indicating the possibility of receptor heterogeneity. A clear indication for the involvement of two distinct receptor sites was evident from the concentration-effect curve to 5-CT, consisting of two distinct phases: pEC$_{50}$=8.8, first phase; pEC$_{50}$=6.8, second phase. This 100-fold difference in EC$_{50}$ values for 5-CT provided a degree of separation sufficient to allow accurate measurements of antagonist-induced shifts for each site without interference from the other. Therefore, 5-CT was used as the agonist in subsequent studies, in which the sites were characterized using antagonists.

Identification of the 5-HT Receptor Subtype Mediating the Low Potency, Second Phase of the Response to 5-CT The second phase of the concentration-effect curve to 5-CT was shifted selectively by 1-naphthylpiperazine (1-NP; 0.01 to 1.0 μM). Schild analysis of this antagonism yielded a $pK_B$ value of 8.5 with a unit slope. (Notably, only the highest concentration of 1-NP (1.0 μM) produced any significant (6.8±0.54 fold) rightward shift of the first phase of the response to 5-CT. A $pK_B$ estimate of 6.8 was determined for the interaction of 1-NP at the first phase. See below.) This affinity is in agreement with that for 1-NP at either a $5\text{-}HT_{2B}$ ($pK_B$=8.3; Wainscott et al., 1993) or $5\text{-}HT_{2C}$ subtype ($pK_B$=8.2; Hoyer, 1989), but is at least 10-fold greater than its affinity for the $5\text{-}HT_{1A}$ ($pK_B$=7.2; Hoyer, 1989), 5-HTLB ($pK_B$=6.6; Hoyer, 1989), $5\text{-}HT_{1E}$ ($pK_B$=6.7; Adham et al., 1993), and $5\text{-}HT_{2A}$ ($pK_B$=7.2; Hoyer, 1989) and $5\text{-}HT_7$ ($pK_B$=7.1; Bard et al., 1993) subtypes.

The second phase of the response to 5-CT was also antagonized by rauwolscine ($pK_B$=7.8). This affinity is in agreement with that of rauwolscine for the $5\text{-}HT_{2B}$ receptor ($pK_B$=7.5; Wainscott et al., 1993), but is at least 10-fold greater than its affinity for the $5\text{-}HT_{1B}$ ($pK_B$=6.0; Hoyer et al., 1994), $5\text{-}HT_{1E}$ ($pK_B$=5.5; Adham et al., 1993), $5\text{-}HT_{2A}$ ($pK_B$=6.1; Hoyer, 1989), and $5\text{-}HT_{2C}$ ($pK_B$=5.8; Hoyer, 1989) subtypes.

The second phase of the response to 5-CT was also antagonized by mesulergine ($pK_B$=7.4). This affinity is in agreement with that for mesulergine at the $5\text{-}HT_{2B}$ receptor ($pK_B$=7.4–7.8; Wainscott et al., 1993), but is at least 10-fold greater than its affinity at the $5\text{-}HT_{1A}$ ($pK_B$=6.2; Hoyer, 1989) subtype. In addition, the affinity is at least 100 fold greater than its affinity for the $5\text{-}HT_{1B}$ ($pK_B$=4.9; Hoyer, 1989), $5\text{-}HT_{1D}$ ($pK_B$=5.2; Hoyer, 1989), $5\text{-}HT_{1F}$ ($pK_B$<5; Adham et al., 1993), $5\text{-}HT_4$ (inactive; Hoyer et al., 1994), $5\text{-}HT_{5A/5B}$ ($pK_B$<6; Hoyer et al., 1994), and $5\text{-}HT_6$ ($pK_B$=5.8; Hoyer et al., 1994) subtypes. Furthermore, its affinity is at least 10 lower than its affinity for the $5\text{-}HT_{2A}$ ($pK_B$=9.1; Hoyer et al., 1994) and $5\text{-}HT_{2C}$ ($pK_B$=9.1; Hoyer et al., 1994) subtypes.

Low potency responses to 5-CT were not affected by pindolol (1 μM; $5\text{-}HT_{1A}$ and $5\text{-}HT_{1B}$-selective), tropisetron (10 μM; $5\text{-}HT_3$ and $5\text{-}HT_4$-selective), or ketanserin (0.1 μM; $5\text{-}HT_{2A}$-selective), confirming that the indicated receptors were not involved. A correlation plot of antagonist affinity estimates ($pK_B$) at this receptor site versus affinity ($pK_I$) at cloned rat $5\text{-}HT_{2B}$ receptor is shown in FIG. 2.

Table 1 (below) shows the $pK_B$ values for a variety of antagonists at the receptor mediating the second phase of the concentration-effect curve to 5-CT, determined from experiments in electrically stimulated bladder strips. Table 1 also lists $pK_I$ values, taken from the indicated reference, for these antagonists at the $5\text{-}HT_{2B}$ receptor.

Figure 2:
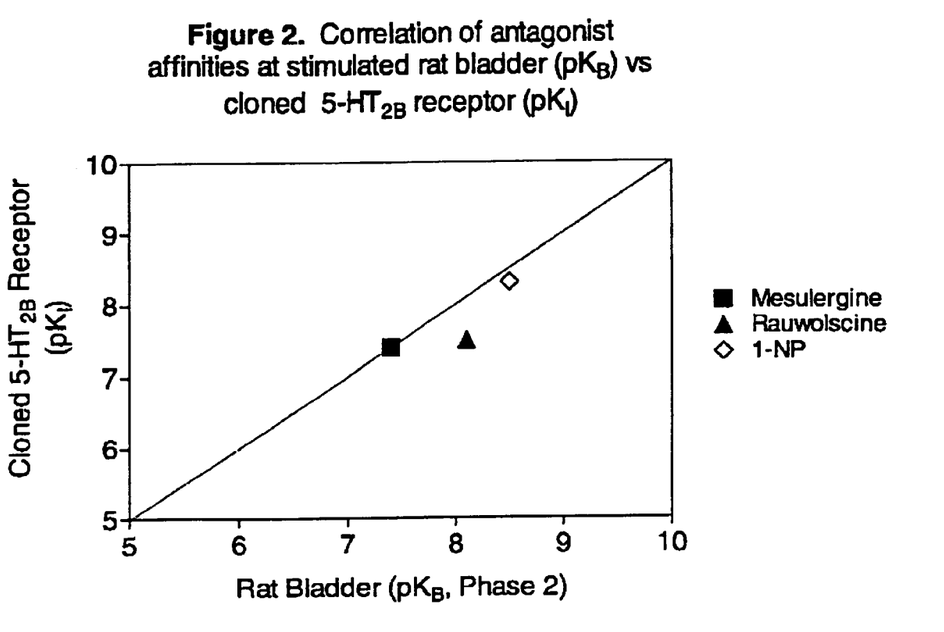

FIG. 2 illustrates the data from Table 1 in a graphical format, showing the correlation between the $pK_B$ values determined from functional experiments in the bladder (abscissa) and $pK_I$ values at the cloned human $5\text{-}HT_{2B}$ receptor (ordinate).

Identification of the 5-HT Receptor Subtype Mediating the High Potency, First Phase of the Response to 5-CT To establish the identity of the receptor mediating the first phase of the response, $pK_B$ values were determined for a variety of selective competitive antagonists and correlated with their published binding affinities for the different 5-HT receptor subtypes. These experiments were conducted in the presence of 0.1 μM 1-NP, a concentration which was found to shift the low potency (second) phase of the concentration-effect curve 100-fold, with no effect on the high potency (first) phase of the curve. This allowed antagonist-induced shifts of the first phase of the response to be measured without interference from the second phase. Furthermore, it should be noted that the insensitivity of the first phase to 0.1 μM 1-NP argues that it cannot be mediated by a $5\text{-}HT_{2B}$ subtype.

Under these conditions the first phase was antagonized in a competitive manner by methiothepin (0.01–0.1 μM; $pK_B$=9.4). This affinity is at least 100-fold greater than that for the $5\text{-}HT_{1A}$ ($pK_B$=7.1; Hoyer, 1989), $5\text{-}HT_{1B}$ ($pK_B$=7.3; Hoyer, 1989), $5\text{-}HT_{1D}$ ($pK_B$=7.3; Hoyer, 1989), $5\text{-}HT_{1E}$ ($pK_B$=6.7; Adham et al., 1993), $5\text{-}HT_{1F}$ ($pK_B$=6.2; Adham et al., 1993), and $5\text{-}HT_{5A}$ ($pK_B$=7.0; Hoyer et al., 1994) subtypes, and is 40-fold greater than that for the $5\text{-}HT_{5B}$ subtype ($pK_B$=7.8; Hoyer et al., 1994).

Similarly, the first phase was antagonized in a competitive manner by mesulergine (0.1–1.0 μM; $pK_B$=7.7). This affinity is at least 100-fold greater than that for the $5\text{-}HT_{1A}$ ($pK_B$=6.2; Hoyer, 1989), $5\text{-}HT_{1B}$ ($pK_B$=4.9; Hoyer, 1989), $5\text{-}HT_{1D}$ ($pK_B$=5.2; Hoyer, 1989), $5\text{-}HT_{1F}$ ($pK_B$<5.0; Adham et al., 1993), $5\text{-}HT_{5A/5B}$ ($pK_B$<6.0; Hoyer et al., 1994), and $5\text{-}HT_6$ ($pK_B$=5.8; Hoyer et al., 1994) subtypes. In addition, it is nearly 30-fold lower than that for the $5\text{-}HT_{2C}$ receptor subtype ($pK_B$=9.1; Hoyer et al., 1994).

Similarly, the first phase was antagonized in a competitive manner by spiperone (1 μM; $pK_B$=7.5). This affinity is at least 100-fold greater than that for the $5\text{-}HT_{1B}$ ($pK_B$=4.4; Hoyer et al., 1994), $5\text{-}HT_{1D}$ ($pK_B$=4.8; Hoyer et al., 1994), $5\text{-}HT_{5A}$ ($pK_B$=5.6; Hoyer et al., 1994), and $5\text{-}HT_{2B}$ ($pK_B$=5.5; Wainscott et al., 1993) receptor subtype. In addition, it is nearly 30-fold greater than that for the $5\text{-}HT_{2C}$ receptor subtype ($pK_B$=5.9; Hoyer, 1989). Furthermore, it is nearly 30-fold lower than that for the $5\text{-}HT_{2A}$ receptor subtype ($pK_B$=9.1; Hoyer et al., 1994).

Similarly, the first phase was antagonized in a competitive manner by rauwolscine (1.0 μM; $pK_B$=6.2). This affinity is more than 10-fold lower than its affinity for the $5\text{-}HT_{2B}$ receptor subtype ($pK_B$=7.5; Wainscott et al., 1993).

In addition, responses were antagonized by the $5\text{-}HT_7$-selective antagonist LY215840 (1.0 μM; $pK_B$=8.2).

When the concentration of 1-NP was increased to 1.0 μM, a significant shift in the first phase was observed, affording a $pK_B$ of 6.6. This affinity is 30 to 100-fold lower than that for the $5\text{-}HT_{2B}$ ($pK_B$=8.3; Wainscott et al., 1993) and $5\text{-}HT_{2C}$ ($pK_B$=8.2; Hoyer, 1989) receptor subtypes.

High potency responses to 5-CT were not affected by pindolol (1 μM; $5\text{-}HT_{1A}$ and $5\text{-}HT_{1B}$-selective), tropisetron (10 μM; $5\text{-}HT_3$ and $5\text{-}HT_4$-selective), or ketanserin (0.1 μM; $5\text{-}HT_{2A}$ and $5\text{-}HT_{2B}$-selective) (Table 2), confirming that the indicated receptors were not involved. A correlation plot of antagonist affinity estimates ($pK_B$) at this receptor site versus affinity ($pK_I$) at cloned human or rat $5\text{-}HT_7$ receptors is shown in FIG. 3.

Table 2 (below) shows the $pK_B$ values for a variety of antagonists at the receptor mediating the first phase of the concentration-effect curve to 5-CT, determined from experiments in electrically stimulated bladder strips. Table 2 also lists $pK_I$ values, taken from the indicated references, for these antagonists at the $5\text{-}HT_7$ receptor.

Figure 3:
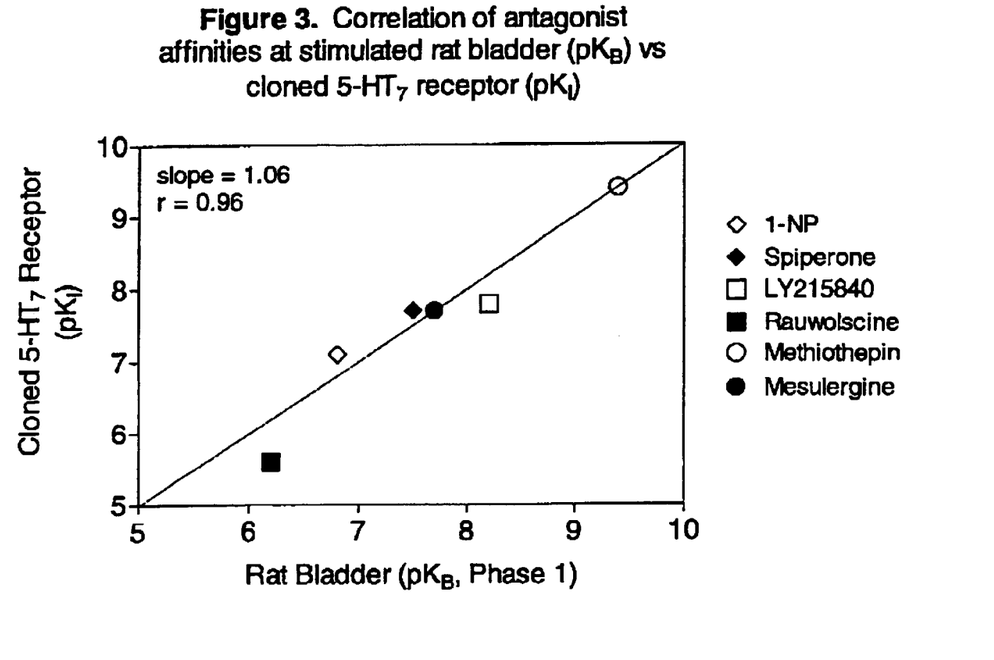

FIG. 3 illustrates the data from Table 2 in a graphical format, showing the significant correlation between the $pK_B$ values determined from functional experiments in the bladder (abscissa) and $pK_I$ values at the cloned human $5\text{-}HT_7$ receptor (ordinate).

Determination of the Site of Action of 5-CT

To investigate whether the actions of 5-CT were mediated pre- or postjunctionally, we assessed the ability of 5-CT to enhance α,β-methylene-ATP-evoked contractions in bladder strips pretreated with tetrodotoxin (0.1 μM) to abolish neuronal activity. In tissues in which the application of α,β-methylene-ATP (3 μM) at 60 min intervals evoked reproducible contractions (ca. ±10%), 5-CT (0.1 and 10 μM; 5 minute incubation) failed to significantly modify the magnitude of a subsequent contraction to α,β-methylene-ATP. The failure of 5-CT to affect the postjunctional response to α,β-methylene-ATP indicates that 5-CT acts to augment electrically evoked contractions by increasing the activity of the parasympathetic neurons in the bladder.

Interpretation of Results

The present results indicate the presence of two pharmacologically distinct 5-HT receptor subtypes in the rat bladder, activation of which facilitates electrically evoked contractions. Based upon quantitative pharmacological characterization, the receptor mediating the lower potency responses has been identified as the $5\text{-HT}_{2B}$ receptor subtype. The receptor mediating the higher potency responses to 5-CT has been identified as the $5\text{-HT}_7$ receptor subtype. These assignments are based on pharmacological data which (1) show a positive correlation with affinity data obtained using the cloned $5\text{-HT}_{2B}$ and $5\text{-HT}_7$ receptors, and (2) exclude all other 5-HT receptor subtypes as having any role in mediating this response (as outlined above).

TABLE 1

Affinity of antagonists determined for inhibition of the second phase of the concentration-effect curve to 5-CT in the rat bladder (PKB), and from radioligand binding studies using the cloned rat $5\text{-HT}_{2B}$ receptor ($pK_I$).

| Antagonist | Conc. (μM) | $PK_B$ | $n^a$ | $pK_I$ | Reference |
|---|---|---|---|---|---|
| Control | — | — | 10 | — | — |
| 1-NP | 1.0 | 8.5 | 5 | 8.3–8.7 | 1 |
| Rauwolscine | 1.0 | 7.8 | 5 | 7.5–7.6 | 1 |
| Mesulergine | 0.1–1.0 | 7.4 | 2 | 7.4–7.8 | 1 |

[a]Number of experiments performed on bladders from different rats.
Reference:
1. Radioligand binding using cloned rat $5\text{-HT}_{2B}$ receptor: Wainscott et al. (1993) Mol. Pharmacol. 43: 419–426

TABLE 2

Affinity of antagonists determined for inhibition of the first phase of the concentration-effect curve to 5-CT in the rat bladder ($pK_B$), and determined from radioligand binding studies using the cloned human or rat $5\text{-HT}_7$ receptor ($pK_I$).

| Antagonist | Conc. (μM) | $pK_B$ | $n^a$ | $pK_I$ | Reference |
|---|---|---|---|---|---|
| Control | — | — | 10 | — | — |
| 1-NP | 1.0 | 6.6 | 5 | 7.1 | 1 |
| Rauwolscine | 1.0 | 6.2 | 5 | 5.6 | this study |
| Mesulergine | 0.1–1.0 | 7.7 | 2 | 7.7 | 1 |
| Spiperone | 1.0 | 7.5 | 4 | 7.7 | 2 |
| Methiophepin | 0.01–0.1 | 9.4 | 3 | 9.4 | 3 |
| LY215840 | 1.0 | 8.2 | 3 | 7.8 | 4 |
| Ketanserin | 1.0 | <6 | 3 | 5.6 | 3 |
| Tropisetron | 10 | <5 | 3 | <4.5 | 2 |
| Pindolol | 1.0 | <6 | 4 | <6 | 2 |

[a]Number of experiments performed on bladders from different rats.
References:
1. Radioligand binding using cloned human $5\text{-HT}_7$ receptor: Bard et al. (1993) J. Biol. Chem. 268, 23422–23426.
2. Radioligand binding using cloned rat $5\text{-HT}_7$ receptor: Ruat et al. (1993) Proc. Natl. Acad. Sci. 90, 8547–8551.
3. Radioligand binding using cloned rat $5\text{-HT}_7$ receptor: Shen et al. (1993) J. Biol. Chem. 268, 18200–18204.
4. Radioligand binding using cloned human $5\text{-HT}_7$ receptor: Cushing et al. (1996) J. Pharmacol. Exp. Ther. 277, 1560–1566.

REFERENCES

Adham, N, Kao, H-T, Schecter, L E Bard, J, Olsen, M, Urquhart, D, Durkin, M, Hartig, P R, Weinshank, R L, Branchek, T A (1993) Cloning of another human serotonin receptor ($5\text{-HT}_{1F}$): A fifth $5\text{-HT}_1$ receptor subtype coupled to the inhibition of adenylate cyclase. Proc. Natl. Acad. Sci. (USA) 90(2):408–412.

Andersson, K-E (1988) Current concepts in the treatment of disorders of micturition. Drugs 35: 477–494.

Andersson, K-E (1996) Neurotransmitters and neuroreceptors in the lower urinary tract. Curr. Opin. Obstet. Gynecol. 5: 361–365.

Ariens, EJ et al. (1960) Receptor reserve and threshold phenomena. Arch. Int. Pharmacdyn. Ther. 127: 459–478.

Arunlakshana, O & Schild, H O (1959) Some quantitative uses of drug antagonism. Brit. J. Pharmacol. 14: 48–58.

Audia, J. E., Baker, S. R., Carrera, J. E., Peteira, C. L., Tercero, C. P. U.S. Pat. No. 5,643,916, issued Jul. 1, 1997 (a).

Audia, J. E., Baker, S. R., Carrera, J. E., Peteira, C. L., Tercero, C. P. U.S. Pat. No. 5,629,317, issued May 13, 1997 (b).

Audia, J. E., Cohen, M. L., Gidda, J. S.., Nelson, D. L. G., Baker, S. R., Ezquerra-Carrera, J., Lamas-Peteira, C., Pedregal-Tercero, C., International Application No. WO 95/24200, published Sep. 14, 1995.

Audia, J. E., Nelson, D. L. G. International Application No. WO 97/35578, published Oct. 2, 1997 (c).

Audia, J. E., Cohen, M. L., Gidda, J. S., Nelson, D. L. G. U.S. Pat. No. 5,688,807, issued Nov. 18, 1997 (d).

Bard, J A, Zgombick, J, Adham, N, Vaysse, P, Branchek, T A, Weinshank, R L (1993) Cloning of a novel human serotonin receptor ($5\text{-HT}_7$) positively linked to adenylate cyclase. J. Biol. Chem. 268: 23422–23426.

Baxter, G. S. (1996) Novel discriminatory ligands for 5-HT (2B) receptors. Behavioural Brain Research 73(1–2): 149–152.

Baxter, G. S., Ellis, E. S., Forbes, I. T., Jones, G. E., Kennett, G. A., Murphy, O. E., Tilford, N. (1995) A potent and selective antagonist at $5\text{-HT}_{2B}$ receptors. Br. J. Pharmacol. 114: 157P.

Bonhaus, D. W., Flippin, L. A., Greenhouse, R. J., Jaime, S., Rocha, C., Dawson, M., Van Natta, K., Chang, L, K., Pulido-Rios, T., Webber, A., Leung, E., Eglen, R. M., Martin, G. R. (1999) RS-127445: a selective, high affinity, orally bioavailable $5\text{-HT}_{2B}$ receptor antagonist. Br. J. Pharmacol. 127(5): 1075–1082.

Chen, H-I (1990) Evidence for the presynaptic action of 5-hydroxytryptamine and in the involvement of purinergic innervation in the rabbit lower urinary tract. Brit. J. Pharmacol. 101: 212–216.

Cheng, Y and Prusoff, W H (1973) Relationship between the inhibition constant (K1) and the concentration of inhibitor which causes 50 percent inhibition (I50) of an enzymatic reaction. Biochem. Pharmacol. 22:3099–3108.

Cleal, A, Corsi, M, Feniuk, W, Gaviraghi, G, Toson, G, Trezise, D & Trist, D (1989) Potentiating action of 5-hydroxytryptamine (5-HT) on electrically-induced contractions in the mouse urinary bladder. *Brit. J. Pharmacol.* 97: 564P.

Cohen, M L (1990) Canine, but not rat bladder contracts to serotonin via activation of 5-$HT_2$ receptors. *J Urology.* 143: 1037–1040.

Cohen, M L & Drey, K (1989) Contractile responses in bladder body, bladder neck and prostate from rat, guinea pig and cat. *J. Pharmacol. Exp. Ther.* 248: 1063–1068.

Corsi, M, Pietra, C, Toson, G, Trist, D, Tuccitto, G & Artibani, W (1991) Pharmacological analysis of 5-hydroxytryptamine effects on electrically stimulated human isolated urinary bladder. *Brit. J. Pharmacol.* 104: 719–725.

Cushing, D J, Zgombick, J M, Nelson, D L, Cohen, M L. LY215840, a high-affinity 5-HT7 receptor ligand, blocks serotonin-induced relaxation in canine coronary artery (1996) *J. Pharmacol. Exp. Ther.* 277: 1560–1566.

Dearry, A, Gingrich, J A, Falardeau, P, Fremeau, R T Jr, Bates, M D, Caron, M G (1990) Molecular cloning and expression of the gene for a human D1 dopamine receptor. Nature 347: 72–76.

Ferguson, D and Christopher, N (1996) Urinaery bladder function and drug development. *Trends Pharmacol. Sci.* 17: 161–165.

Forbes, I. T., International Application No. WO 97/29097, published Aug. 14, 1997.

Forbes, I. T. and Rahman, S. K., International Application No. WO 97/49695, published Dec. 31, 1997.

Forbes, I. T., Dabbs, S., Duckworth, D. M., Jennings, A. J., King, F. D., Lovell, P. J., Brown, A. M., Collin, L., Hagan, J. J., Middlemiss, D. N., Riley, G. J., Thomas, D. R., and Upton, N. (1998) (R)-3,N-Dimethyl-N-[1-methyl-3-(4-methyl-piperidin-1-yl)propyl]benzenesulfonamide: The First Selective 5-$HT_7$ Receptor Antagonist. *J. of Medicinal Chemistry* 41(5): 655–657.

Forbes, I. T., Jones, G. E., Murphy, O. E., Holland, V., Baxter, G. S. (1995) N-(1-methyl-5-indolyl) N'-(3-methyl-5-isothiazolyl)urea: a novel, high-affinity 5-$HT_{2B}$ receptor antagonist. *J. Med. Chem.* 38(6): 855–857.

Furchgott, R (1972) The classification of adrenoceptors (adrenergic receptors). An evaluation from the standpoint of receptor theory. *In: Handbook of Experimental Pharmacology* 33: 283–335.

Godel, T. and Hunkeler, W., International Application No. WO 99/24022, published May 20, 1999.

Holt, S E, Cooper, M & Wyllie, J H (1985) Evidence for purinergic transmission in mouse bladder and for modulation of responses to electrical stimulation by 5-hydroxytryptamine. *European J. Pharmacol.* 116: 105–111.

Holt, S E, Cooper, M & Wyllie, J H (1986) On the nature of the receptor mediating the action of 5-hydroxytryptamine in potentiating responses of the mouse urinary bladder strip to electrical stimulation. *Naunyn-Schmeidegergs Arch. Pharmacol.* 334: 333–340.

Hoyer, D (1989) 5-Hydroxytryptamine receptors and effector coupling mechanisms in peripheral tissues. In: The Peripheral Actions of 5-Hydroxytryptamine, Ed. J. R. Fozard. Oxford Medical Publications, pp 74–75.

Hoyer, D, Clarke, D, Fozard, J, Hartig, P, Martin, G, Mylecharane, E, Saxena, P and Humphrey, P (1994) VIII International Union of Pharmacology Classification of Receptors for 5-Hydroxytryptamine (Serotonin). *Pharmacological Reviews* 46: 157–203.

Kenakin, T P (1987) In: Pharmacological Analysis of Drug-Receptor Interaction. Raven Press, New York, pp. 190–192.

Kennett, G. A., Ainsworth, K., Trail, B., Blackburn, T. P. (1997) BW 723C86, a 5-$HT_{2B}$ receptor agonist, causes hyperphagia and reduced grooming in rats. *Neuropharm.* 36(2): 233–239.

Kennett, G. A., Bright, F., Trail, B., Baxter, G. S., Blackburn, T. P. (1996) Effects of the 5-$HT_{2B}$ receptor agonist, BW 723C86, on three rat models of anxiety. *Br. J. Pharm.* 117: 1443–1448.

Kikuchi, C., Nagaso, H., Hiranuma, T., and Koyama, M. (1999) Tetrahydrobenzindoles: Selective Antagonists of the 5-$HT_7$ Receptor. *J. of Medicinal Chemistry* 42(4): 533–535.

Klarskov, P and Høorby-Petersen (1986) Influence of serotonin on lower urinary tract smooth muscle in vitro. *British Journal of Urology* 58: 507–513.

Koyama, M., Kikuchi, C., Ushiroda, O., Ando, T., Nagaso, H., Fuji, K., Okuno, M., and Hiranuma, T., International Application No. WO 98/00400, published Jan. 8, 1998.

Lopata, M A, Cleveland, D W, Sollner-Webb, B (1984) High level transient expression of a chloramphenicol acetyl transferase gene by DEAE-dextran mediated DNA transfection coupled with a dimethyl sulfoxide or glycerol shock treatment. *Nucleic Acids Res.* 12: 5707–5717.

May, J. A. and Sharif, N. A., International Application No. WO 99/59499, published Nov. 25, 1999.

Messori, E, Rizzi, C A, Candura, S M, Lucchelli, A, Balestra, B. Tonini, M (1995) 5-Hydroxytryptamine receptors that facilitate excitatory neuromuscular transmission in the guinea-pig isolated detrusor muscle. *Br. J. Pharmacol.* 115: 677–683.

Ohnmacht, C J, Russell, K, Empfield, J R, Frank, C A, Gibson, K H, Mayhugh, D R, McLaren, F M, Shapiro, H S, Brown, F J, Trainor, D A, Ceccarelli, C, Lin, M M, Masek, B B, Forst, J M, Harris, R J, Hulsizer, J M, Lewis, J J, Silverman, S M, Smith, R W, Warwick, P J, Kau, S T, Chun, A L, Grant, T L, Howe, B B, Neilson K L, et al 1996) N-aryl-3,3,3-trifluoro-2-hydroxy-2-methylpropanamides: KATP potassium channel openers. Modifications on the western region. *J. Med. Chem.* 39(23):4592–4601.

Ruat, M, Traiffort, E, Leurs, R, Tardivel-Lacombe, J, Diaz, J, Arrang, J M, and Schwartz, J C (1993) Molecular cloning, characterization, and localization of a high-affinity serotonin receptor (5-$HT_7$) activating cAMP formation. *Proc. Natl. Acad. Sci.* 90: 8547–8551.

Saxena, P R, Heiligers, J, Mylecharane, E J, Tio, R (1985) Excitatory 5-hydroxytryptamine receptors in the cat urinary bladder are of the M- and 5-$HT_2$-type. *J. Auton. Pharmacol.* 5: 101–107.

Shen, Y, Monsma, F J Jr, Metcalf M A, Jose P A, Hamblin M W, Sibley D R (1993) Molecular cloning and expression of a 5-hydroxytryptamine7 serotonin receptor subtype. *J. Biol. Chem.* 268: 18200–18204.

Sokoloff, P, Giros, B, Martres, M P, Bouthenet, M L, Schwartz, J C (1990) Molecular cloning and characterization of a novel dopamine receptor (D3) as a target for neuroleptics. *Nature* 347: 146–151.

Sunahara, R K, Guan, H C, O'Dowd B F, Seeman, P, Laurier, L G, Ng, G, George, S R, Torchia, J, Van Tol, H H, Niznik, H B (1991) Cloning of a gene for a human dopamine D5 receptor with higher affinity for dopamine than D1. *Nature* 350: 614–619.

Swami, S K and Abrams P (1996) Urge Incontinence. *Urodynamics II* 23: 417–425.

Tonini, M, Messori, E, Franceschetti, G P, Rizzi, C A, Castoldi, A F, Coccini, T, Candura, S M (1994) Characterization of the 5-HT receptor potentiating neuromuscular cholinergic transmission in strips of human isolated detrusor muscle. *Br. J. Pharmacol.* 113: 1–2.

Waikar, M V, Ford, A P D W & Clarke, D E (1994) Evidence for an inhibitory 5-HT$_4$ receptor in urinary bladder of Rhesus and Cynomolgus monkeys. *Brit. J. Pharmacol.* 111: 213≧218.

Wainscott, D B, Cohen, M L, Schenck, K W, Audia, J E, Nissen, J S, Baez, M, Kursar, J D, Lucaites, V L, Nelson, D L (1993) Pharmacological characteristics of the newly cloned rat 5-hydroxytryptamine$_{2F}$ receptor. *Mol. Pharmacol.* 43(3): 419–426.

Wein, A J (1987) Lower urinary tract function and pharmacologic management of lower urinary tract dysfunction. *Current Medical Therapy for Urologic Disease* 14: 273–296.

Werkstrom, V, Ny, L, Persson, K, Andersson, K E (1997) Neurotransmitter release evoked by alpha-latrotoxin in the smooth muscle of the female pig urethra. *Naunyn Schmiedebergs Arch. Pharmacol.* 356: 151–158.

Zgombick, J M, Weinshank, R L, Macchi, M, Schechter, L E, Branchek, T A, Hartig, P R (1991) Expression and pharmacological characterization of a canine 5-hydroxytryptamine 1D receptor subtype. *Mol. Pharmacol.* 40: 1036–1042.

PCT International Application No. WO 95/24200, Method For Treating 5HT$_{2B}$ Receptor Related Conditions, International Publication Date, Sep. 14, 1995.

PCT International Application No. WO 97/35578, Tetrahydro-Beta-Carboline Compounds, International Publication Date, Oct. 21, 1997.

What is claimed is:

1. A method of treating urinary incontinence in a subject which comprises administering to the subject a therapeutically effective amount of a 5-HT$_7$ antagonist which binds to the human 5-HT$_7$ receptor with an affinity at least ten-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

2. The method of claim 1, wherein the 5-HT$_7$ antagonist additionally binds to the human 5-HT$_7$ receptor with an affinity at least ten-fold higher than the affinity with which it binds to each of the human 5-HT$_7$, 5-HT$_{1D}$, 5-HT$_{1E}$, 5-HT$_{1F}$, 5-HT$_{5A}$, and 5-HT$_{5B}$ receptors.

3. The method of claim 1, wherein the 5-HT$_7$ antagonist also binds to the human 5-HT$_7$ receptor with an affinity at least ten-fold higher than the affinity with which it binds to any human $\alpha_2$ adrenoceptor or any human $\beta$ adrenoceptor.

4. The method of claim 1, wherein the 5-HT$_7$ antagonist also binds to the human 5-HT$_7$ receptor with an affinity at least ten-fold higher than the affinity with which it binds to the human histamine H$_1$ and H$_2$ receptors.

5. The method of claim 1, wherein the 5-HT$_7$ antagonist also binds to the human 5-HT$_7$ receptor with an affinity at least ten-fold higher than the affinity with which it binds to the human dopamine D$_1$, D$_2$, D$_3$, and D$_5$ receptors.

6. The method of claim 1, wherein the 5-HT$_7$ antagonist also binds to the human 5-HT$_7$ receptor with an affinity at least ten-fold higher than the affinity with which it binds to the human $\alpha_{1A}$ adrenoceptor and the human $\alpha_{1B}$ adrenoceptor.

7. The method of claim 1, wherein the 5-HT$_7$ antagonist binds to the human 5-HT$_7$ receptor with an affinity at least 50-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

8. The method of claim 7, wherein the 5-HT$_7$ antagonist binds to the human 5-HT$_7$ receptor with an affinity at least 100-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

9. The method of claim 8, wherein the 5-HT$_7$ antagonist binds to the human 5-HT$_7$ receptor with an affinity at least 200-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

10. The method of claim 1, wherein the 5-HT$_7$ antagonist is also a 5-HT$_{2B}$ antagonist which binds to the human 5-HT$_{2B}$ receptor with an affinity at least 10-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

11. The method of claim 10, wherein the 5-HT$_7$ antagonist additionally binds to the human 5-HT$_{2B}$ receptor with an affinity at least ten-fold higher than the affinity with which it binds to each of the human 5-HT$_{1B}$, 5-HT$_{1D}$, 5-HT$_{1E}$, 5-HT$_{1F}$, 5-HT$_{5A}$, and 5-HT$_{5B}$ receptors.

12. The method of claim 10, wherein the 5-HT$_7$ antagonist binds to the human 5-HT$_{2B}$ receptor with an affinity at least 50-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

13. The method of claim 12, wherein the 5-HT$_7$ antagonist binds to the human 5-HT$_{2B}$ receptor with an affinity at least 100-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

14. The method of claim 13, wherein the 5-HT$_7$ antagonist binds to the human 5-HT$_{2B}$ receptor with an affinity at least 200-fold higher than the affinity with which it binds to each of the human 5-HT$_{1A}$, 5-HT$_{2A}$, 5-HT$_{2C}$, 5-HT$_3$, 5-HT$_4$, and 5-HT$_6$ receptors.

15. The method of claim 10, wherein the 5-HT$_7$ antagonist is a 5-HT$_{2B}$ antagonist which binds to the human 5-HT$_{2B}$ receptor with an affinity at least ten-fold higher than the affinity with which it binds to any human $\alpha_2$ adrenoceptor or any human $\beta$ adrenoceptor.

16. The method of claim 10, wherein the 5-HT$_7$ antagonist is a 5-HT$_{2B}$ antagonist which binds to the human 5-HT$_{2B}$ receptor with an affinity at least ten-fold higher than the affinity with which it binds to the human histamine H$_1$ and H$_2$ receptors.

17. The method of claim 10, wherein the 5-HT$_7$ antagonist is a 5-HT$_{2B}$ antagonist which binds to the human 5-HT$_{2B}$ receptor with an affinity at least ten-fold higher than the affinity with which it binds to the human dopamine D$_1$, D$_2$, D$_3$, and D$_5$ receptors.

18. The method of claim 10, wherein the 5-HT$_7$ antagonist is a 5-HT$_{2B}$ antagonist which binds to the human 5-HT$_{2B}$ receptor with an affinity at least ten-fold higher than the affinity with which it binds to the human $\alpha_{1A}$ adrenoceptor and the human $\beta_{1B}$ adrenoceptor.

* * * * *